(12) United States Patent
Sanborn et al.

(10) Patent No.: US 8,597,198 B2
(45) Date of Patent: *Dec. 3, 2013

(54) WORK OF BREATHING DISPLAY FOR A VENTILATION SYSTEM

(75) Inventors: Warren G. Sanborn, Escondido, CA (US); Peter R. Doyle, Vista, CA (US)

(73) Assignee: Covidien LP, Mansfield, MA (US)

( * ) Notice: Subject to any disclaimer, the term of this patent is extended or adjusted under 35 U.S.C. 154(b) by 36 days.

This patent is subject to a terminal disclaimer.

(21) Appl. No.: 13/117,644

(22) Filed: May 27, 2011

(65) Prior Publication Data

US 2011/0230780 A1   Sep. 22, 2011

Related U.S. Application Data

(63) Continuation of application No. 11/408,457, filed on Apr. 21, 2006, now Pat. No. 8,021,310.

(51) Int. Cl.
*A61B 5/08* (2006.01)

(52) U.S. Cl.
USPC .......................................... 600/538; 600/529

(58) Field of Classification Search
USPC ................................................. 600/529–543
See application file for complete search history.

(56) References Cited

U.S. PATENT DOCUMENTS

| | | | |
|---|---|---|---|
| 3,577,984 A | 5/1971 | Levy et al. | |
| 3,659,590 A | 5/1972 | Jones et al. | |
| 3,703,893 A | 11/1972 | Hardway, Jr. | |
| 3,871,371 A | 3/1975 | Weigl | |
| 3,940,742 A | 2/1976 | Hudspeth et al. | |
| 3,961,624 A | 6/1976 | Weigl | |
| 3,961,627 A | 6/1976 | Ernst et al. | |
| 3,977,394 A | 8/1976 | Jones et al. | |
| 3,991,304 A | 11/1976 | Hillsman | |
| 3,996,928 A | 12/1976 | Marx | |
| 4,034,743 A | 7/1977 | Greenwood et al. | |
| 4,036,217 A | 7/1977 | Ito et al. | |
| 4,053,951 A | 10/1977 | Hudspeth et al. | |
| 4,090,513 A | 5/1978 | Togawa | |
| 4,112,931 A | 9/1978 | Burns | |
| 4,187,842 A | 2/1980 | Schreiber | |
| 4,215,409 A | 7/1980 | Strowe | |
| 4,241,739 A | 12/1980 | Elson | |
| 4,258,718 A | 3/1981 | Goldman | |

(Continued)

FOREIGN PATENT DOCUMENTS

| | | |
|---|---|---|
| EP | 0414777 | 3/1991 |
| EP | 1421966 | 5/2004 |

(Continued)

OTHER PUBLICATIONS

7200 Series Ventilator, Options, and Accessories: Operator's Manual. Nellcor Puritan Bennett, Part No. 22300 A, Sep. 1990, pp. 1-196.

(Continued)

*Primary Examiner* — Michael Kahelin
*Assistant Examiner* — Karen Toth

(57) ABSTRACT

A breathing support system is provided. The system may include a breathing support device configured to deliver gas to a patient and a display device associated with the breathing support device. The display device may be configured to display a graphic indicating one or more measures regarding the patient's work of breathing.

21 Claims, 9 Drawing Sheets

(56) References Cited

U.S. PATENT DOCUMENTS

| | | |
|---|---|---|
| 4,296,756 A | 10/1981 | Dunning et al. |
| 4,308,872 A | 1/1982 | Watson et al. |
| 4,323,064 A | 4/1982 | Hoenig et al. |
| 4,326,513 A | 4/1982 | Schulz et al. |
| 4,391,283 A | 7/1983 | Sharpless et al. |
| 4,401,115 A | 8/1983 | Monnier |
| 4,401,116 A | 8/1983 | Fry et al. |
| 4,407,295 A | 10/1983 | Steuer et al. |
| 4,440,177 A | 4/1984 | Anderson et al. |
| 4,444,201 A | 4/1984 | Itoh |
| 4,463,764 A | 8/1984 | Anderson et al. |
| 4,473,081 A | 9/1984 | Dioguardi et al. |
| 4,495,944 A | 1/1985 | Brisson et al. |
| 4,537,190 A | 8/1985 | Caillot et al. |
| 4,550,726 A | 11/1985 | McEwen |
| 4,579,115 A | 4/1986 | Wallroth et al. |
| 4,637,385 A | 1/1987 | Rusz |
| 4,654,029 A | 3/1987 | D'Antonio |
| 4,736,750 A | 4/1988 | Valdespino et al. |
| 4,752,089 A | 6/1988 | Carter |
| 4,790,327 A | 12/1988 | Despotis |
| 4,796,639 A | 1/1989 | Snow et al. |
| 4,813,409 A | 3/1989 | Ismach |
| 4,852,582 A | 8/1989 | Pell |
| 4,867,152 A | 9/1989 | Kou et al. |
| 4,876,903 A | 10/1989 | Budinger |
| 4,917,108 A | 4/1990 | Mault |
| 4,921,642 A | 5/1990 | LaTorraca |
| 4,954,799 A | 9/1990 | Kumar |
| 4,984,158 A | 1/1991 | Hillsman |
| 4,990,894 A | 2/1991 | Loescher et al. |
| 5,003,985 A | 4/1991 | White et al. |
| 5,004,472 A | 4/1991 | Wallace |
| 5,009,662 A | 4/1991 | Wallace et al. |
| 5,020,527 A | 6/1991 | Dessertine |
| 5,021,046 A | 6/1991 | Wallace |
| 5,057,822 A | 10/1991 | Hoffman |
| 5,058,601 A | 10/1991 | Riker |
| 5,072,737 A | 12/1991 | Goulding |
| 5,107,830 A | 4/1992 | Younes |
| 5,137,026 A | 8/1992 | Waterson et al. |
| 5,150,291 A | 9/1992 | Cummings et al. |
| 5,161,525 A | 11/1992 | Kimm et al. |
| 5,163,423 A | 11/1992 | Suzuki |
| 5,167,506 A | 12/1992 | Kilis et al. |
| 5,203,343 A | 4/1993 | Axe et al. |
| 5,224,487 A | 7/1993 | Bellofatto et al. |
| 5,231,981 A | 8/1993 | Schreiber et al. |
| 5,235,973 A | 8/1993 | Levinson |
| 5,237,987 A | 8/1993 | Anderson et al. |
| 5,246,010 A | 9/1993 | Gazzara et al. |
| 5,251,632 A | 10/1993 | Delpy |
| 5,261,397 A | 11/1993 | Grunstein |
| 5,261,415 A | 11/1993 | Dussault |
| 5,271,389 A | 12/1993 | Isaza et al. |
| 5,277,195 A | 1/1994 | Williams |
| 5,279,304 A | 1/1994 | Einhorn et al. |
| 5,279,549 A | 1/1994 | Ranford |
| 5,293,875 A | 3/1994 | Stone |
| 5,299,568 A | 4/1994 | Forare et al. |
| 5,301,921 A | 4/1994 | Kumar |
| 5,303,698 A | 4/1994 | Tobia et al. |
| 5,303,699 A | 4/1994 | Bonassa et al. |
| 5,307,795 A | 5/1994 | Whitwam et al. |
| 5,316,009 A * | 5/1994 | Yamada .................. 600/533 |
| 5,319,355 A | 6/1994 | Russek |
| 5,319,540 A | 6/1994 | Isaza et al. |
| 5,325,861 A | 7/1994 | Goulding |
| 5,333,106 A | 7/1994 | Lanpher et al. |
| 5,333,606 A | 8/1994 | Schneider et al. |
| 5,339,807 A | 8/1994 | Carter |
| 5,339,825 A | 8/1994 | McNaughton et al. |
| 5,343,857 A | 9/1994 | Schneider et al. |
| 5,351,522 A | 10/1994 | Lura |
| 5,355,893 A | 10/1994 | Mick et al. |
| 5,357,946 A | 10/1994 | Kee et al. |
| 5,357,975 A | 10/1994 | Kraemer et al. |
| 5,363,842 A | 11/1994 | Mishelevich et al. |
| 5,365,922 A | 11/1994 | Raemer |
| 5,368,019 A | 11/1994 | LaTorraca |
| 5,373,851 A | 12/1994 | Reinhold, Jr. et al. |
| 5,383,449 A | 1/1995 | Forare et al. |
| 5,383,470 A | 1/1995 | Kolbly |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,404,871 A | 4/1995 | Goodman et al. |
| 5,407,174 A | 4/1995 | Kumar |
| 5,413,110 A | 5/1995 | Cummings et al. |
| 5,438,980 A | 8/1995 | Phillips |
| 5,442,940 A | 8/1995 | Secker et al. |
| 5,443,075 A | 8/1995 | Holscher |
| 5,445,160 A | 8/1995 | Culver et al. |
| 5,446,449 A | 8/1995 | Lhomer et al. |
| 5,448,996 A | 9/1995 | Bellin et al. |
| 5,452,714 A | 9/1995 | Anderson et al. |
| 5,456,264 A | 10/1995 | Series et al. |
| 5,464,410 A | 11/1995 | Skeens et al. |
| 5,479,939 A | 1/1996 | Ogino |
| 5,487,731 A | 1/1996 | Denton |
| 5,495,848 A | 3/1996 | Aylsworth et al. |
| 5,501,231 A | 3/1996 | Kaish |
| 5,507,291 A | 4/1996 | Stirbl et al. |
| 5,513,631 A | 5/1996 | McWilliams |
| 5,517,983 A | 5/1996 | Deighan et al. |
| 5,517,985 A | 5/1996 | Kirk et al. |
| 5,518,002 A | 5/1996 | Wolf et al. |
| 5,520,071 A | 5/1996 | Jones |
| 5,524,615 A | 6/1996 | Power |
| 5,531,221 A | 7/1996 | Power |
| 5,534,851 A | 7/1996 | Russek |
| 5,537,992 A | 7/1996 | Bjoernstijerna et al. |
| 5,542,410 A | 8/1996 | Goodman et al. |
| 5,542,415 A | 8/1996 | Brady |
| 5,544,674 A | 8/1996 | Kelly |
| 5,549,106 A | 8/1996 | Gruenke et al. |
| 5,549,117 A | 8/1996 | Tacklind et al. |
| 5,553,620 A | 9/1996 | Snider et al. |
| 5,558,086 A | 9/1996 | Smith et al. |
| 5,560,353 A | 10/1996 | Willemot et al. |
| 5,564,414 A | 10/1996 | Walker et al. |
| 5,564,432 A | 10/1996 | Thomson |
| 5,571,142 A | 11/1996 | Brown et al. |
| 5,575,283 A | 11/1996 | Sjoestrand |
| 5,582,167 A | 12/1996 | Joseph |
| 5,590,648 A | 1/1997 | Mitchell et al. |
| 5,591,130 A | 1/1997 | Denton |
| 5,596,984 A | 1/1997 | O'Mahony et al. |
| 5,606,976 A | 3/1997 | Marshall et al. |
| 5,611,335 A | 3/1997 | Makhoul et al. |
| 5,626,144 A | 5/1997 | Tacklind et al. |
| 5,630,411 A | 5/1997 | Holscher |
| 5,632,270 A | 5/1997 | O'Mahoney et al. |
| 5,632,281 A | 5/1997 | Rayburn |
| 5,634,461 A | 6/1997 | Faithfull et al. |
| 5,634,471 A | 6/1997 | Fairfax et al. |
| 5,642,735 A | 7/1997 | Kolbly |
| 5,645,048 A | 7/1997 | Brodsky et al. |
| 5,647,346 A | 7/1997 | Holscher |
| 5,651,264 A | 7/1997 | Lo et al. |
| 5,655,516 A | 8/1997 | Goodman et al. |
| 5,660,168 A | 8/1997 | Ottosson et al. |
| 5,660,171 A | 8/1997 | Kimm et al. |
| 5,664,560 A | 9/1997 | Merrick et al. |
| 5,664,562 A | 9/1997 | Bourdon |
| 5,669,379 A | 9/1997 | Somerson et al. |
| 5,671,767 A | 9/1997 | Kelly |
| 5,672,041 A | 9/1997 | Ringdahl et al. |
| 5,673,689 A | 10/1997 | Power |
| 5,676,129 A | 10/1997 | Rocci, Jr. et al. |
| 5,676,132 A | 10/1997 | Tillotson et al. |
| 5,678,539 A | 10/1997 | Schubert et al. |
| 5,683,424 A | 11/1997 | Brown et al. |

(56) References Cited

U.S. PATENT DOCUMENTS

| | | |
|---|---|---|
| 5,692,497 A | 12/1997 | Schnitzer et al. |
| 5,704,346 A | 1/1998 | Inoue |
| 5,704,366 A | 1/1998 | Tacklind et al. |
| 5,704,367 A | 1/1998 | Ishikawa et al. |
| 5,706,801 A | 1/1998 | Remes et al. |
| 5,715,812 A | 2/1998 | Deighan et al. |
| 5,724,990 A | 3/1998 | Ogino |
| 5,730,140 A | 3/1998 | Fitch |
| 5,730,145 A | 3/1998 | Defares et al. |
| 5,735,287 A | 4/1998 | Thomson |
| 5,738,092 A | 4/1998 | Mock et al. |
| 5,740,792 A | 4/1998 | Ashley et al. |
| 5,743,267 A | 4/1998 | Nikolic et al. |
| 5,752,506 A | 5/1998 | Richardson |
| 5,752,509 A | 5/1998 | Lachmann et al. |
| 5,755,218 A | 5/1998 | Johansson et al. |
| 5,758,652 A | 6/1998 | Nikolic |
| 5,762,480 A | 6/1998 | Adahan |
| 5,771,884 A | 6/1998 | Yarnall et al. |
| 5,778,874 A | 7/1998 | Maguire et al. |
| 5,791,339 A | 8/1998 | Winter |
| 5,794,612 A | 8/1998 | Wachter et al. |
| 5,794,986 A | 8/1998 | Gansel et al. |
| 5,800,361 A | 9/1998 | Rayburn |
| 5,806,514 A | 9/1998 | Mock et al. |
| 5,809,997 A | 9/1998 | Wolf |
| 5,813,397 A | 9/1998 | Goodman et al. |
| 5,813,399 A | 9/1998 | Isaza et al. |
| 5,819,723 A | 10/1998 | Joseph |
| 5,822,715 A | 10/1998 | Worthington et al. |
| 5,826,570 A | 10/1998 | Goodman et al. |
| 5,826,575 A | 10/1998 | Lall |
| 5,827,179 A | 10/1998 | Lichter et al. |
| 5,829,441 A | 11/1998 | Kidd et al. |
| 5,839,430 A | 11/1998 | Cama |
| 5,864,938 A | 2/1999 | Gansel et al. |
| 5,865,168 A | 2/1999 | Isaza |
| 5,865,171 A | 2/1999 | Cinquin |
| 5,865,174 A | 2/1999 | Kloeppel |
| 5,875,777 A | 3/1999 | Eriksson |
| 5,878,744 A | 3/1999 | Pfeiffer |
| 5,881,717 A | 3/1999 | Isaza |
| 5,881,723 A | 3/1999 | Wallace et al. |
| 5,884,622 A | 3/1999 | Younes |
| 5,884,623 A | 3/1999 | Winter |
| 5,891,023 A | 4/1999 | Lynn |
| 5,899,203 A | 5/1999 | Defares et al. |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,921,920 A | 7/1999 | Marshall et al. |
| 5,924,418 A | 7/1999 | Lewis |
| 5,931,160 A | 8/1999 | Gilmore et al. |
| 5,932,812 A | 8/1999 | Delsing |
| 5,934,274 A | 8/1999 | Merrick et al. |
| 5,937,854 A | 8/1999 | Stenzler |
| 5,956,501 A | 9/1999 | Brown |
| 5,957,861 A | 9/1999 | Combs et al. |
| 5,971,937 A | 10/1999 | Ekstrom |
| 5,975,081 A | 11/1999 | Hood et al. |
| 5,979,440 A | 11/1999 | Honkonen et al. |
| 5,980,466 A | 11/1999 | Thomson |
| 6,012,450 A | 1/2000 | Rubsamen |
| 6,017,315 A | 1/2000 | Starr et al. |
| 6,024,089 A | 2/2000 | Wallace et al. |
| 6,026,323 A | 2/2000 | Skladnev et al. |
| 6,032,119 A | 2/2000 | Brown et al. |
| 6,041,780 A | 3/2000 | Richard et al. |
| 6,047,860 A | 4/2000 | Sanders |
| 6,055,506 A | 4/2000 | Frasca, Jr. |
| 6,073,110 A | 6/2000 | Rhodes et al. |
| 6,076,523 A | 6/2000 | Jones et al. |
| 6,099,481 A | 8/2000 | Daniels et al. |
| 6,106,481 A | 8/2000 | Cohen |
| 6,116,240 A | 9/2000 | Merrick et al. |
| 6,116,464 A | 9/2000 | Sanders |
| 6,118,847 A | 9/2000 | Hernandez-Guerra et al. |
| 6,119,684 A | 9/2000 | Nohl et al. |
| 6,123,073 A | 9/2000 | Schlawin et al. |
| 6,135,106 A | 10/2000 | Dirks et al. |
| 6,142,150 A | 11/2000 | O'Mahony et al. |
| 6,148,814 A | 11/2000 | Clemmer et al. |
| 6,148,815 A | 11/2000 | Wolf |
| 6,155,257 A | 12/2000 | Lurie et al. |
| 6,158,432 A | 12/2000 | Biondi et al. |
| 6,159,147 A | 12/2000 | Lichter et al. |
| 6,161,539 A | 12/2000 | Winter |
| 6,162,183 A | 12/2000 | Hoover |
| 6,167,362 A | 12/2000 | Brown et al. |
| 6,168,568 B1 | 1/2001 | Gavriely |
| 6,171,264 B1 | 1/2001 | Bader |
| 6,176,833 B1 | 1/2001 | Thomson |
| 6,186,956 B1 | 2/2001 | McNamee |
| 6,190,326 B1 | 2/2001 | McKinnon et al. |
| 6,192,876 B1 | 2/2001 | Denyer et al. |
| 6,198,963 B1 | 3/2001 | Haim et al. |
| 6,199,550 B1 | 3/2001 | Wiesmann et al. |
| 6,202,642 B1 | 3/2001 | McKinnon et al. |
| 6,213,955 B1 | 4/2001 | Karakasoglu et al. |
| 6,220,245 B1 | 4/2001 | Takabayashi et al. |
| 6,223,744 B1 | 5/2001 | Garon |
| 6,224,553 B1 | 5/2001 | Nevo |
| 6,233,539 B1 | 5/2001 | Brown |
| 6,234,963 B1 | 5/2001 | Blike et al. |
| 6,240,920 B1 | 6/2001 | Strom |
| 6,251,082 B1 | 6/2001 | Rayburn |
| 6,261,238 B1 | 7/2001 | Gavriely |
| 6,269,810 B1 | 8/2001 | Brooker et al. |
| 6,269,812 B1 | 8/2001 | Wallace et al. |
| 6,273,088 B1 | 8/2001 | Hillsman |
| 6,273,444 B1 | 8/2001 | Power |
| 6,279,574 B1 | 8/2001 | Richardson et al. |
| 6,283,119 B1 | 9/2001 | Bourdon |
| 6,283,923 B1 | 9/2001 | Finkelstein et al. |
| 6,287,264 B1 | 9/2001 | Hoffman |
| 6,301,497 B1 | 10/2001 | Neustadter |
| 6,302,106 B1 | 10/2001 | Lewis |
| 6,305,373 B1 | 10/2001 | Wallace et al. |
| 6,321,748 B1 | 11/2001 | O'Mahoney |
| 6,322,502 B1 | 11/2001 | Schoenberg et al. |
| 6,325,785 B1 | 12/2001 | Babkes et al. |
| 6,339,410 B1 | 1/2002 | Milner et al. |
| 6,340,348 B1 | 1/2002 | Krishnan et al. |
| 6,342,040 B1 | 1/2002 | Starr et al. |
| 6,349,722 B1 | 2/2002 | Gradon et al. |
| 6,349,724 B1 | 2/2002 | Burton et al. |
| 6,355,002 B1 | 3/2002 | Faram et al. |
| 6,357,438 B1 | 3/2002 | Hansen |
| 6,360,745 B1 | 3/2002 | Wallace et al. |
| 6,362,620 B1 | 3/2002 | Debbins et al. |
| 6,367,475 B1 | 4/2002 | Kofoed et al. |
| 6,369,838 B1 | 4/2002 | Wallace et al. |
| 6,370,419 B1 | 4/2002 | Lampotang et al. |
| 6,377,046 B1 | 4/2002 | Debbins et al. |
| 6,379,301 B1 | 4/2002 | Worthington et al. |
| 6,390,088 B1 | 5/2002 | Nohl et al. |
| 6,390,091 B1 * | 5/2002 | Banner et al. ............ 128/204.21 |
| 6,390,092 B1 | 5/2002 | Leenhoven |
| 6,390,977 B1 | 5/2002 | Faithfull et al. |
| 6,402,698 B1 | 6/2002 | Mault |
| 6,408,043 B1 | 6/2002 | Hu et al. |
| 6,412,483 B1 | 7/2002 | Jones et al. |
| 6,415,792 B1 | 7/2002 | Schoolman |
| 6,416,471 B1 | 7/2002 | Kumar et al. |
| 6,421,650 B1 | 7/2002 | Goetz et al. |
| 6,427,687 B1 | 8/2002 | Kirk |
| 6,435,175 B1 | 8/2002 | Stenzler |
| 6,436,053 B1 | 8/2002 | Knapp, II et al. |
| 6,439,229 B1 | 8/2002 | Du et al. |
| 6,450,164 B1 | 9/2002 | Banner et al. |
| 6,454,708 B1 | 9/2002 | Ferguson et al. |

(56) References Cited

U.S. PATENT DOCUMENTS

| | | |
|---|---|---|
| 6,459,933 B1 | 10/2002 | Lurie et al. |
| 6,463,930 B2 | 10/2002 | Biondi et al. |
| 6,467,478 B1 | 10/2002 | Merrick et al. |
| 6,471,658 B1 | 10/2002 | Daniels et al. |
| 6,488,029 B1 | 12/2002 | Hood et al. |
| 6,488,629 B1 | 12/2002 | Saetre et al. |
| RE37,970 E | 1/2003 | Costello, Jr. |
| 6,511,426 B1 | 1/2003 | Hossack et al. |
| 6,512,938 B2 | 1/2003 | Claure et al. |
| 6,515,683 B1 | 2/2003 | Wright |
| 6,517,497 B2 | 2/2003 | Rymut et al. |
| 6,533,723 B1 | 3/2003 | Lockery et al. |
| 6,533,730 B2 | 3/2003 | Strom |
| 6,543,449 B1 | 4/2003 | Woodring et al. |
| 6,543,701 B1 | 4/2003 | Ho |
| 6,544,192 B2 | 4/2003 | Starr et al. |
| 6,546,930 B1 | 4/2003 | Emerson et al. |
| 6,547,728 B1 | 4/2003 | Cornuejols |
| 6,553,991 B1 | 4/2003 | Isaza |
| 6,553,992 B1 | 4/2003 | Berthon-Jones et al. |
| 6,557,553 B1 | 5/2003 | Borrello |
| 6,557,554 B1 | 5/2003 | Sugiura |
| 6,566,875 B1 | 5/2003 | Hasson et al. |
| 6,571,122 B2 | 5/2003 | Schroeppel et al. |
| 6,571,795 B2 | 6/2003 | Bourdon |
| 6,571,796 B2 | 6/2003 | Banner et al. |
| 6,578,575 B1 | 6/2003 | Jonson |
| 6,581,592 B1 | 6/2003 | Bathe et al. |
| 6,584,973 B1 | 7/2003 | Biondi et al. |
| 6,597,939 B1 | 7/2003 | Lampotang et al. |
| 6,599,252 B2 | 7/2003 | Starr |
| 6,603,494 B1 | 8/2003 | Banks et al. |
| 6,606,993 B1 | 8/2003 | Wiesmann et al. |
| 6,620,106 B2 | 9/2003 | Mault |
| 6,621,917 B1 | 9/2003 | Vilser |
| 6,622,726 B1 | 9/2003 | Du |
| 6,629,934 B2 | 10/2003 | Mault et al. |
| 6,630,176 B2 | 10/2003 | Li et al. |
| 6,644,310 B1 | 11/2003 | Delache et al. |
| 6,644,312 B2 | 11/2003 | Berthon-Jones et al. |
| 6,645,158 B2 | 11/2003 | Mault |
| 6,650,346 B1 | 11/2003 | Jaeger et al. |
| 6,651,653 B1 | 11/2003 | Honkonen et al. |
| 6,656,129 B2 | 12/2003 | Niles et al. |
| 6,668,824 B1 | 12/2003 | Isaza et al. |
| 6,668,829 B2 | 12/2003 | Biondi et al. |
| 6,671,529 B2 | 12/2003 | Claure et al. |
| 6,673,018 B2 | 1/2004 | Friedman |
| 6,675,801 B2 | 1/2004 | Wallace et al. |
| 6,679,258 B1 | 1/2004 | Strom |
| 6,681,764 B1 | 1/2004 | Honkonen et al. |
| 6,698,423 B1 | 3/2004 | Honkonen et al. |
| 6,707,476 B1 | 3/2004 | Hochstedler |
| 6,708,688 B1 | 3/2004 | Rubin et al. |
| 6,709,405 B2 | 3/2004 | Jonson |
| 6,712,762 B1 | 3/2004 | Lichter et al. |
| 6,718,974 B1 | 4/2004 | Moberg |
| 6,718,975 B2 | 4/2004 | Blomberg |
| 6,725,077 B1 | 4/2004 | Balloni et al. |
| 6,725,447 B1 | 4/2004 | Gilman et al. |
| 6,725,860 B2 | 4/2004 | Wallroth et al. |
| 6,733,449 B1 | 5/2004 | Krishnamurthy et al. |
| 6,738,079 B1 | 5/2004 | Kellerman et al. |
| 6,739,337 B2 | 5/2004 | Isaza |
| 6,740,046 B2 | 5/2004 | Knapp, II et al. |
| 6,743,172 B1 | 6/2004 | Blike |
| 6,744,374 B1 | 6/2004 | Kuenzner |
| 6,745,764 B2 | 6/2004 | Hickle |
| 6,755,193 B2 | 6/2004 | Berthon-Jones et al. |
| 6,755,787 B2 | 6/2004 | Hossack et al. |
| 6,760,610 B2 | 7/2004 | Tschupp et al. |
| 6,761,167 B1 | 7/2004 | Nadjafizadeh et al. |
| 6,761,168 B1 | 7/2004 | Nadjafizadeh et al. |
| 6,776,159 B2 | 8/2004 | Pelerossi et al. |
| 6,782,888 B1 | 8/2004 | Friberg et al. |
| 6,790,178 B1 | 9/2004 | Mault et al. |
| 6,792,066 B1 | 9/2004 | Harder et al. |
| 6,796,305 B1 | 9/2004 | Banner et al. |
| 6,801,227 B2 | 10/2004 | Bocionek et al. |
| 6,801,802 B2 | 10/2004 | Sitzman et al. |
| 6,805,118 B2 | 10/2004 | Brooker et al. |
| 6,807,965 B1 | 10/2004 | Hickle |
| 6,814,074 B1 | 11/2004 | Nadjafizadeh et al. |
| 6,820,614 B2 | 11/2004 | Bonutti |
| 6,820,618 B2 | 11/2004 | Banner et al. |
| 6,822,223 B2 | 11/2004 | Davis |
| 6,824,520 B2 | 11/2004 | Orr et al. |
| 6,828,910 B2 | 12/2004 | VanRyzin et al. |
| 6,830,046 B2 | 12/2004 | Blakley et al. |
| 6,834,647 B2 | 12/2004 | Blair et al. |
| 6,837,242 B2 | 1/2005 | Younes |
| 6,839,753 B2 | 1/2005 | Biondi et al. |
| 6,845,773 B2 | 1/2005 | Berthon-Jones et al. |
| 6,858,006 B2 | 2/2005 | MacCarter et al. |
| 6,860,266 B2 | 3/2005 | Blike |
| 6,866,040 B1 | 3/2005 | Bourdon |
| 6,866,629 B2 | 3/2005 | Bardy |
| 6,893,397 B2 | 5/2005 | Bardy |
| 6,899,103 B1 | 5/2005 | Hood et al. |
| 6,899,683 B2 | 5/2005 | Mault et al. |
| 6,899,684 B2 | 5/2005 | Mault et al. |
| 6,910,481 B2 | 6/2005 | Kimmel et al. |
| 6,921,369 B1 | 7/2005 | Gehrke et al. |
| 6,923,079 B1 | 8/2005 | Snibbe |
| 6,931,269 B2 | 8/2005 | Terry |
| 6,932,083 B2 | 8/2005 | Jones et al. |
| 6,932,767 B2 | 8/2005 | Landry et al. |
| 6,947,780 B2 | 9/2005 | Scharf |
| 6,951,541 B2 | 10/2005 | Desmarais |
| 6,954,702 B2 | 10/2005 | Pierry et al. |
| 6,956,572 B2 | 10/2005 | Zaleski |
| 6,960,854 B2 | 11/2005 | Nadjafizadeh et al. |
| 6,970,919 B1 | 11/2005 | Doi et al. |
| 6,976,958 B2 | 12/2005 | Quy |
| 6,986,347 B2 | 1/2006 | Hickle |
| 6,997,185 B2 | 2/2006 | Han et al. |
| 6,997,880 B2 | 2/2006 | Carlebach et al. |
| 7,008,380 B1 | 3/2006 | Rees et al. |
| 7,017,574 B2 | 3/2006 | Biondi et al. |
| 7,019,652 B2 | 3/2006 | Richardson |
| 7,033,323 B2 | 4/2006 | Botbol et al. |
| 7,036,504 B2 | 5/2006 | Wallace et al. |
| 7,039,878 B2 | 5/2006 | Auer et al. |
| 7,040,315 B1 | 5/2006 | Strömberg |
| 7,040,318 B2 | 5/2006 | Däscher et al. |
| 7,040,321 B2 | 5/2006 | Göbel |
| 7,046,254 B2 | 5/2006 | Brown et al. |
| 7,047,092 B2 | 5/2006 | Wimsatt |
| 7,051,736 B2 | 5/2006 | Banner et al. |
| 7,062,251 B2 | 6/2006 | Birkett et al. |
| 7,066,173 B2 | 6/2006 | Banner et al. |
| 7,077,125 B2 | 7/2006 | Scheuch |
| 7,077,131 B2 | 7/2006 | Hansen |
| 7,081,091 B2 | 7/2006 | Merrett et al. |
| 7,081,095 B2 | 7/2006 | Lynn et al. |
| RE39,225 E | 8/2006 | Isaza et al. |
| 7,083,574 B2 | 8/2006 | Kline |
| 7,089,927 B2 | 8/2006 | John et al. |
| 7,089,937 B2 | 8/2006 | Berthon-Jones et al. |
| 7,094,208 B2 | 8/2006 | Williams et al. |
| 7,116,810 B2 | 10/2006 | Miller et al. |
| 7,117,438 B2 | 10/2006 | Wallace et al. |
| 7,128,578 B2 | 10/2006 | Lampotang et al. |
| 7,147,600 B2 | 12/2006 | Bardy |
| 7,156,808 B2 | 1/2007 | Quy |
| 7,162,296 B2 | 1/2007 | Leonhardt et al. |
| 7,164,972 B2 | 1/2007 | Imhof et al. |
| 7,165,221 B2 | 1/2007 | Monteleone et al. |
| 7,169,112 B2 | 1/2007 | Caldwell |
| 7,172,557 B1 | 2/2007 | Parker |
| 7,182,083 B2 | 2/2007 | Yanof et al. |
| 7,187,790 B2 | 3/2007 | Sabol et al. |
| 7,188,621 B2 | 3/2007 | DeVries et al. |
| 7,201,734 B2 | 4/2007 | Hickle |

(56) References Cited

U.S. PATENT DOCUMENTS

| | | | |
|---|---|---|---|
| 7,203,353 B2 | 4/2007 | Klotz et al. |
| 7,210,478 B2 | 5/2007 | Banner et |
| 7,211,049 B2 | 5/2007 | Bradley et |
| 7,219,666 B2 | 5/2007 | Friberg et al. |
| 7,220,230 B2 | 5/2007 | Roteliuk et al. |
| 7,222,054 B2 | 5/2007 | Geva |
| 7,223,965 B2 | 5/2007 | Davis |
| 7,228,323 B2 | 6/2007 | Angerer et al. |
| 7,241,269 B2 | 7/2007 | McCawley et al. |
| 7,246,618 B2 | 7/2007 | Habashi |
| 7,247,154 B2 | 7/2007 | Hickle |
| 7,252,640 B2 | 8/2007 | Ni et al. |
| 7,261,690 B2 | 8/2007 | Teller et al. |
| 7,264,730 B2 | 9/2007 | Connell et al. |
| 7,270,126 B2 | 9/2007 | Wallace et al. |
| 7,275,540 B2 | 10/2007 | Bolam et al. |
| 7,278,579 B2 | 10/2007 | Loffredo et al. |
| 7,282,032 B2 | 10/2007 | Miller |
| 7,285,090 B2 | 10/2007 | Stivoric et al. |
| 7,294,105 B1 | 11/2007 | Islam |
| 7,294,112 B1 | 11/2007 | Dunlop |
| 7,298,280 B2 | 11/2007 | Voege et al. |
| 7,300,418 B2 | 11/2007 | Zaleski |
| 7,303,680 B2 | 12/2007 | Connell et al. |
| 7,308,550 B2 | 12/2007 | Cornett |
| 7,310,551 B1 | 12/2007 | Koh et al. |
| 7,310,720 B2 | 12/2007 | Cornett |
| 7,311,665 B2 | 12/2007 | Hawthorne et al. |
| 7,314,451 B2 | 1/2008 | Halperin et al. |
| 7,316,231 B2 | 1/2008 | Hickle |
| 7,318,808 B2 | 1/2008 | Tarassenko et al. |
| 7,318,892 B2 | 1/2008 | Connell et al. |
| 7,321,802 B2 | 1/2008 | Wasner et al. |
| 7,322,352 B2 | 1/2008 | Minshull et al. |
| 7,322,937 B2 | 1/2008 | Blomberg et al. |
| 7,331,340 B2 | 2/2008 | Barney |
| 7,333,969 B2 | 2/2008 | Lee et al. |
| 7,334,578 B2 | 2/2008 | Biondi et al. |
| 7,343,916 B2 | 3/2008 | Biondo et al. |
| 7,343,917 B2 | 3/2008 | Jones |
| 7,347,200 B2 | 3/2008 | Jones et al. |
| 7,347,207 B2 | 3/2008 | Ahlmen et al. |
| 7,351,340 B2 | 4/2008 | Connell et al. |
| 7,362,341 B2 | 4/2008 | McGuire et al. |
| 7,367,337 B2 | 5/2008 | Berthon-Jones et al. |
| 7,367,955 B2 | 5/2008 | Zhang et al. |
| 7,369,757 B2 | 5/2008 | Farbarik |
| 7,370,650 B2 | 5/2008 | Nadjafizadeh et al. |
| 7,374,535 B2 | 5/2008 | Schoenberg et al. |
| 7,377,276 B2 | 5/2008 | Roy et al. |
| 7,380,210 B2 | 5/2008 | Lontka et al. |
| RE40,365 E | 6/2008 | Kirchgeorg et al. |
| 7,383,148 B2 | 6/2008 | Ahmed |
| 7,387,610 B2 | 6/2008 | Stahmann et al. |
| 7,413,546 B2 | 8/2008 | Agutter et al. |
| 7,422,562 B2 | 9/2008 | Hatib et al. |
| 7,425,201 B2 | 9/2008 | Euliano et al. |
| 7,428,902 B2 | 9/2008 | Du et al. |
| 7,435,220 B2 | 10/2008 | Ranucci |
| 7,438,072 B2 | 10/2008 | Izuchukwu |
| 7,438,073 B2 | 10/2008 | Delache et al. |
| 7,448,383 B2 | 11/2008 | Delache et al. |
| 7,452,333 B2 | 11/2008 | Roteliuk |
| 7,460,959 B2 | 12/2008 | Jafari |
| 7,464,339 B2 | 12/2008 | Keenan, Jr. et al. |
| 7,469,698 B1 | 12/2008 | Childers et al. |
| 7,487,773 B2 | 2/2009 | Li |
| 7,487,774 B2 | 2/2009 | Acker |
| 7,490,085 B2 | 2/2009 | Walker et al. |
| 7,496,400 B2 | 2/2009 | Hoskonen et al. |
| 7,500,481 B2 | 3/2009 | Delache et al. |
| 7,504,954 B2 | 3/2009 | Spaeder |
| 7,512,450 B2 | 3/2009 | Ahmed |
| 7,512,593 B2 | 3/2009 | Karklins et al. |
| 7,527,053 B2 | 5/2009 | DeVries et al. |
| 7,527,054 B2 | 5/2009 | Misholi |
| 7,530,353 B2 | 5/2009 | Choncholas et al. |
| RE40,806 E | 6/2009 | Gradon et al. |
| 7,543,582 B2 | 6/2009 | Lu et al. |
| 7,548,833 B2 | 6/2009 | Ahmed |
| 7,552,731 B2 | 6/2009 | Jorczak et al. |
| 7,556,036 B2 | 7/2009 | Bouillon et al. |
| 7,559,903 B2 | 7/2009 | Moussavi et al. |
| 7,562,657 B2 | 7/2009 | Blanch et al. |
| 7,565,905 B2 | 7/2009 | Hickle |
| 7,584,712 B2 | 9/2009 | Lu |
| 7,590,551 B2 | 9/2009 | Auer |
| 7,597,099 B2 | 10/2009 | Jones et al. |
| 7,603,170 B2 | 10/2009 | Hatlestad et al. |
| 7,603,631 B2 | 10/2009 | Bermudez et al. |
| 7,606,668 B2 | 10/2009 | Pierry et al. |
| 7,609,138 B2 | 10/2009 | Dietrich et al. |
| 7,610,915 B2 | 11/2009 | Dittmann |
| 7,618,378 B2 | 11/2009 | Bingham et al. |
| 7,625,345 B2 | 12/2009 | Quinn |
| 7,630,755 B2 | 12/2009 | Stahmann et al. |
| 7,650,181 B2 | 1/2010 | Freeman et al. |
| 7,652,571 B2 | 1/2010 | Parkulo et al. |
| 7,654,802 B2 | 2/2010 | Crawford, Jr. et al. |
| 7,654,966 B2 | 2/2010 | Westinskow et al. |
| 7,658,188 B2 | 2/2010 | Halpern et al. |
| 7,662,106 B2 | 2/2010 | Daniels et al. |
| 7,668,579 B2 | 2/2010 | Lynn |
| 7,669,598 B2 | 3/2010 | Rick et al. |
| 7,671,733 B2 | 3/2010 | McNeal et al. |
| 7,678,063 B2 | 3/2010 | Felmlee et al. |
| 7,682,312 B2 | 3/2010 | Lurie |
| 7,684,931 B2 | 3/2010 | Pierry et al. |
| 7,693,697 B2 | 4/2010 | Westenskow et al. |
| 7,694,677 B2 | 4/2010 | Tang |
| 7,698,156 B2 | 4/2010 | Martucci et al. |
| 7,708,015 B2 | 5/2010 | Seeger et al. |
| 7,717,112 B2 | 5/2010 | Sun et al. |
| 7,717,113 B2 | 5/2010 | Andrieux |
| D618,356 S | 6/2010 | Ross |
| 7,731,663 B2 | 6/2010 | Averina et al. |
| 7,736,132 B2 | 6/2010 | Bliss et al. |
| 7,740,013 B2 | 6/2010 | Ishizaki et al. |
| 7,753,049 B2 | 7/2010 | Jorczak et al. |
| 7,766,012 B2 | 8/2010 | Scheuch et al. |
| 7,771,364 B2 | 8/2010 | Arbel et al. |
| 7,772,965 B2 | 8/2010 | Farhan et al. |
| 7,778,709 B2 | 8/2010 | Gollasch et al. |
| 7,778,851 B2 | 8/2010 | Schoenberg et al. |
| 7,784,461 B2 | 8/2010 | Figueiredo et al. |
| 7,785,263 B2 | 8/2010 | Roteliuk et al. |
| 7,785,265 B2 | 8/2010 | Schätzl |
| 7,793,659 B2 | 9/2010 | Breen |
| 7,793,660 B2 | 9/2010 | Kimmel et al. |
| 7,810,497 B2 | 10/2010 | Pittman et al. |
| 7,814,906 B2 | 10/2010 | Moretti |
| 7,819,815 B2 | 10/2010 | Younes |
| 7,823,588 B2 | 11/2010 | Hansen |
| 7,831,450 B2 | 11/2010 | Schoenberg et al. |
| 7,832,394 B2 | 11/2010 | Schechter et al. |
| 7,836,882 B1 | 11/2010 | Rumph et al. |
| 7,837,629 B2 | 11/2010 | Bardy |
| 7,850,619 B2 | 12/2010 | Gavish et al. |
| 7,855,656 B2 | 12/2010 | Maschke |
| 7,855,716 B2 | 12/2010 | McCreary et al. |
| 7,859,401 B2 | 12/2010 | Falck et al. |
| 7,866,317 B2 | 1/2011 | Muellinger et al. |
| 7,871,394 B2 | 1/2011 | Halbert et al. |
| D632,796 S | 2/2011 | Ross et al. |
| D632,797 S | 2/2011 | Ross et al. |
| 7,881,780 B2 | 2/2011 | Flaherty |
| 7,883,480 B2 | 2/2011 | Dunlop |
| 7,885,828 B2 | 2/2011 | Glaser-Seidnitzer et al. |
| 7,886,231 B2 | 2/2011 | Hopermann et al. |
| 7,891,353 B2 | 2/2011 | Chalvignac |
| 7,891,354 B2 | 2/2011 | Farbarik |
| 7,893,560 B2 | 2/2011 | Carter |
| 7,895,527 B2 | 2/2011 | Zaleski et al. |
| 7,909,033 B2 | 3/2011 | Faram |

(56) References Cited

U.S. PATENT DOCUMENTS

| | | |
|---|---|---|
| 7,912,537 B2 | 3/2011 | Lee et al. |
| 7,927,286 B2 | 4/2011 | Ranucci |
| 7,931,601 B2 | 4/2011 | Ranucci |
| D638,852 S | 5/2011 | Skidmore et al. |
| 7,953,419 B2 | 5/2011 | Jost et al. |
| 7,956,719 B2 | 6/2011 | Anderson, Jr. et al. |
| 7,958,892 B2 | 6/2011 | Kwok et al. |
| 7,970,450 B2 | 6/2011 | Kroecker et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 * | 9/2011 | Sanborn et al. ............ 600/538 |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2001/0056358 A1 | 12/2001 | Dulong et al. |
| 2002/0026941 A1 | 3/2002 | Biondi et al. |
| 2002/0044059 A1 | 4/2002 | Reeder et al. |
| 2002/0077863 A1 | 6/2002 | Rutledge et al. |
| 2002/0091548 A1 | 7/2002 | Auer et al. |
| 2002/0177758 A1 | 11/2002 | Schoenberg et al. |
| 2003/0060723 A1 | 3/2003 | Joo et al. |
| 2003/0062045 A1 | 4/2003 | Woodring et al. |
| 2003/0106553 A1 | 6/2003 | Vanderveen |
| 2003/0130567 A1 | 7/2003 | Mault et al. |
| 2003/0130595 A1 | 7/2003 | Mault |
| 2003/0140928 A1 | 7/2003 | Bui et al. |
| 2003/0140929 A1 | 7/2003 | Wilkes et al. |
| 2003/0141368 A1 | 7/2003 | Pascual et al. |
| 2003/0141981 A1 | 7/2003 | Bui et al. |
| 2003/0144878 A1 | 7/2003 | Wilkes et al. |
| 2003/0144880 A1 | 7/2003 | Talachian et al. |
| 2003/0144881 A1 | 7/2003 | Talachian et al. |
| 2003/0144882 A1 | 7/2003 | Talachian et al. |
| 2003/0201697 A1 | 10/2003 | Richardson |
| 2003/0204414 A1 | 10/2003 | Wilkes et al. |
| 2003/0204416 A1 | 10/2003 | Radpay et al. |
| 2003/0204419 A1 | 10/2003 | Wilkes et al. |
| 2003/0204420 A1 | 10/2003 | Wilkes et al. |
| 2003/0208152 A1 | 11/2003 | Avrahami et al. |
| 2003/0208465 A1 | 11/2003 | Yurko et al. |
| 2003/0222548 A1 | 12/2003 | Richardson et al. |
| 2003/0230308 A1 | 12/2003 | Linden |
| 2004/0010425 A1 | 1/2004 | Wilkes et al. |
| 2004/0034289 A1 | 2/2004 | Teller et al. |
| 2004/0040560 A1 * | 3/2004 | Euliano et al. ......... 128/204.23 |
| 2004/0059604 A1 | 3/2004 | Zaleski |
| 2004/0073453 A1 | 4/2004 | Nenov et al. |
| 2004/0078231 A1 | 4/2004 | Wilkes et al. |
| 2004/0121767 A1 | 6/2004 | Simpson et al. |
| 2004/0122294 A1 | 6/2004 | Hatlestad et al. |
| 2004/0150525 A1 | 8/2004 | Wilson et al. |
| 2004/0167465 A1 | 8/2004 | Mihai et al. |
| 2004/0167804 A1 | 8/2004 | Simpson et al. |
| 2004/0172222 A1 | 9/2004 | Simpson et al. |
| 2004/0172300 A1 | 9/2004 | Mihai et al. |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0224293 A1 | 11/2004 | Penning et al. |
| 2004/0236240 A1 | 11/2004 | Kraus et al. |
| 2004/0249673 A1 | 12/2004 | Smith |
| 2005/0016534 A1 | 1/2005 | Ost |
| 2005/0033198 A1 | 2/2005 | Kehyayan et al. |
| 2005/0039748 A1 | 2/2005 | Andrieux |
| 2005/0054910 A1 | 3/2005 | Tremblay et al. |
| 2005/0055242 A1 | 3/2005 | Bello et al. |
| 2005/0055244 A1 | 3/2005 | Mullan et al. |
| 2005/0065817 A1 | 3/2005 | Mihai et al. |
| 2005/0075542 A1 | 4/2005 | Goldreich |
| 2005/0075904 A1 | 4/2005 | Wager et al. |
| 2005/0085869 A1 | 4/2005 | Tehrani et al. |
| 2005/0104860 A1 | 5/2005 | McCreary |
| 2005/0108057 A1 | 5/2005 | Cohen et al. |
| 2005/0112013 A1 | 5/2005 | DeVries et al. |
| 2005/0112325 A1 | 5/2005 | Hickle |
| 2005/0124866 A1 | 6/2005 | Elaz et al. |
| 2005/0133027 A1 | 6/2005 | Elaz et al. |
| 2005/0137480 A1 | 6/2005 | Alt et al. |
| 2005/0139212 A1 | 6/2005 | Bourdon |
| 2005/0139213 A1 | 6/2005 | Blike |
| 2005/0143632 A1 | 6/2005 | Elaz et al. |
| 2005/0156933 A1 | 7/2005 | Lee et al. |
| 2005/0171876 A1 | 8/2005 | Golden |
| 2005/0177096 A1 | 8/2005 | Bollish et al. |
| 2005/0188083 A1 | 8/2005 | Biondi et al. |
| 2005/0192488 A1 | 9/2005 | Bryenton et al. |
| 2005/0204310 A1 | 9/2005 | De Zwart et al. |
| 2005/0215904 A1 | 9/2005 | Sumanaweera et al. |
| 2005/0217674 A1 | 10/2005 | Burton et al. |
| 2005/0242034 A1 | 11/2005 | Connell et al. |
| 2005/0251040 A1 | 11/2005 | Relkuntwar et al. |
| 2005/0288571 A1 | 12/2005 | Perkins et al. |
| 2006/0047202 A1 | 3/2006 | Elliott |
| 2006/0078867 A1 | 4/2006 | Penny et al. |
| 2006/0080140 A1 | 4/2006 | Buttner et al. |
| 2006/0080343 A1 | 4/2006 | Carter et al. |
| 2006/0102171 A1 | 5/2006 | Gavish |
| 2006/0122474 A1 | 6/2006 | Teller et al. |
| 2006/0129055 A1 | 6/2006 | Orr et al. |
| 2006/0144396 A1 | 7/2006 | DeVries et al. |
| 2006/0149144 A1 | 7/2006 | Lynn et al. |
| 2006/0149589 A1 | 7/2006 | Wager |
| 2006/0150982 A1 | 7/2006 | Wood |
| 2006/0155183 A1 | 7/2006 | Kroecker |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0173257 A1 | 8/2006 | Nagai et al. |
| 2006/0174884 A1 | 8/2006 | Habashi |
| 2006/0178911 A1 | 8/2006 | Syed et al. |
| 2006/0189880 A1 | 8/2006 | Lynn et al. |
| 2006/0189900 A1 | 8/2006 | Flaherty |
| 2006/0195041 A1 | 8/2006 | Lynn et al. |
| 2006/0196507 A1 | 9/2006 | Bradley |
| 2006/0200009 A1 | 9/2006 | Wekell et al. |
| 2006/0213518 A1 | 9/2006 | DeVries et al. |
| 2006/0229822 A1 | 10/2006 | Theobald et al. |
| 2006/0235324 A1 | 10/2006 | Lynn |
| 2006/0237015 A1 | 10/2006 | Berthon-Jones et al. |
| 2006/0249151 A1 | 11/2006 | Gambone |
| 2006/0249153 A1 | 11/2006 | DeVries et al. |
| 2006/0264762 A1 | 11/2006 | Starr |
| 2006/0278221 A1 | 12/2006 | Schermeier et al. |
| 2006/0278222 A1 | 12/2006 | Schermeier et al. |
| 2006/0293609 A1 | 12/2006 | Stahmann et al. |
| 2006/0294464 A1 | 12/2006 | Tokimoto et al. |
| 2007/0000490 A1 | 1/2007 | DeVries et al. |
| 2007/0000494 A1 | 1/2007 | Banner et al. |
| 2007/0016441 A1 | 1/2007 | Stroup |
| 2007/0017515 A1 | 1/2007 | Wallace et al. |
| 2007/0021673 A1 | 1/2007 | Arbel et al. |
| 2007/0028921 A1 | 2/2007 | Banner et al. |
| 2007/0038081 A1 | 2/2007 | Eck et al. |
| 2007/0060812 A1 | 3/2007 | Harel et al. |
| 2007/0062532 A1 | 3/2007 | Choncholas |
| 2007/0062533 A1 | 3/2007 | Choncholas et al. |
| 2007/0073181 A1 | 3/2007 | Pu et al. |

(56) References Cited

U.S. PATENT DOCUMENTS

| | | |
|---|---|---|
| 2007/0077200 A1 | 4/2007 | Baker |
| 2007/0113849 A1 | 5/2007 | Matthews et al. |
| 2007/0119453 A1 | 5/2007 | Lu et al. |
| 2007/0123758 A1 | 5/2007 | Miesel et al. |
| 2007/0123792 A1 | 5/2007 | Kline |
| 2007/0129647 A1 | 6/2007 | Lynn |
| 2007/0149860 A1 | 6/2007 | Lynn et al. |
| 2007/0156060 A1 | 7/2007 | Cervantes |
| 2007/0156456 A1 | 7/2007 | McGillin et al. |
| 2007/0157931 A1 | 7/2007 | Parker et al. |
| 2007/0163589 A1 | 7/2007 | DeVries et al. |
| 2007/0179357 A1 | 8/2007 | Bardy |
| 2007/0185390 A1 | 8/2007 | Perkins et al. |
| 2007/0191697 A1 | 8/2007 | Lynn et al. |
| 2007/0199566 A1 | 8/2007 | Be'eri |
| 2007/0208438 A1 | 9/2007 | El-Mankabady et al. |
| 2007/0215155 A1 | 9/2007 | Marx et al. |
| 2007/0225574 A1 | 9/2007 | Ueda |
| 2007/0227537 A1 | 10/2007 | Bemister et al. |
| 2007/0229249 A1 | 10/2007 | McNeal |
| 2007/0241884 A1 | 10/2007 | Yamazaki et al. |
| 2007/0265510 A1 | 11/2007 | Bardy |
| 2007/0265877 A1 | 11/2007 | Rice et al. |
| 2007/0271122 A1 | 11/2007 | Zaleski |
| 2007/0272241 A1 | 11/2007 | Sanborn et al. |
| 2007/0272242 A1 | 11/2007 | Sanborn et al. |
| 2007/0273216 A1 | 11/2007 | Farbarik |
| 2007/0276439 A1 | 11/2007 | Miesel et al. |
| 2007/0284361 A1 | 12/2007 | Nadjafizadeh et al. |
| 2007/0293741 A1 | 12/2007 | Bardy |
| 2008/0000477 A1 | 1/2008 | Huster et al. |
| 2008/0000479 A1 | 1/2008 | Elaz et al. |
| 2008/0007396 A1 | 1/2008 | Parkulo |
| 2008/0033661 A1 | 2/2008 | Syroid et al. |
| 2008/0039735 A1 | 2/2008 | Hickerson |
| 2008/0041380 A1 | 2/2008 | Wallace et al. |
| 2008/0045844 A1 | 2/2008 | Arbel et al. |
| 2008/0047554 A1 | 2/2008 | Roy et al. |
| 2008/0053438 A1 | 3/2008 | DeVries et al. |
| 2008/0053441 A1 | 3/2008 | Gottlib et al. |
| 2008/0064963 A1 | 3/2008 | Schwaibold et al. |
| 2008/0065420 A1 | 3/2008 | Tirinato et al. |
| 2008/0066753 A1 | 3/2008 | Martin et al. |
| 2008/0072896 A1 | 3/2008 | Setzer et al. |
| 2008/0072900 A1 | 3/2008 | Kenyon et al. |
| 2008/0072901 A1 | 3/2008 | Habashi |
| 2008/0072902 A1 | 3/2008 | Setzer et al. |
| 2008/0076970 A1 | 3/2008 | Foulis et al. |
| 2008/0076992 A1 | 3/2008 | Hete |
| 2008/0077033 A1 | 3/2008 | Figueiredo |
| 2008/0077038 A1 | 3/2008 | McDonough et al. |
| 2008/0077436 A1 | 3/2008 | Muradia |
| 2008/0078390 A1 | 4/2008 | Milne et al. |
| 2008/0083644 A1 | 4/2008 | Janbakhsh et al. |
| 2008/0091122 A1 | 4/2008 | Dunlop |
| 2008/0092043 A1 | 4/2008 | Trethewey |
| 2008/0092894 A1 | 4/2008 | Nicolazzi et al. |
| 2008/0097234 A1 | 4/2008 | Nicolazzi et al. |
| 2008/0103368 A1 | 5/2008 | Craine et al. |
| 2008/0110460 A1 | 5/2008 | Elaz et al. |
| 2008/0125873 A1 | 5/2008 | Payne et al. |
| 2008/0161653 A1 | 7/2008 | Lin et al. |
| 2008/0172249 A1 | 7/2008 | Glaser-Seidnitzer |
| 2008/0178880 A1 | 7/2008 | Christopher et al. |
| 2008/0178882 A1 | 7/2008 | Christopher et al. |
| 2008/0183057 A1 | 7/2008 | Taube |
| 2008/0185009 A1 | 8/2008 | Choncholas et al. |
| 2008/0205427 A1 | 8/2008 | Jost |
| 2008/0208012 A1 | 8/2008 | Ali |
| 2008/0214947 A1 | 9/2008 | Hunt et al. |
| 2008/0230057 A1 | 9/2008 | Sutherland |
| 2008/0236582 A1 | 10/2008 | Tehrani |
| 2008/0236585 A1 | 10/2008 | Parker et al. |
| 2008/0243016 A1 | 10/2008 | Liao et al. |
| 2008/0251070 A1 | 10/2008 | Pinskiy et al. |
| 2008/0255880 A1 | 10/2008 | Beller et al. |
| 2008/0258929 A1 | 10/2008 | Maschke |
| 2008/0270912 A1 | 10/2008 | Booth |
| 2008/0281219 A1 | 11/2008 | Glickman et al. |
| 2008/0293025 A1 | 11/2008 | Zamierowsi et al. |
| 2008/0295830 A1 | 12/2008 | Martonen et al. |
| 2008/0295839 A1 | 12/2008 | Habashi |
| 2008/0306351 A1 | 12/2008 | Izumi |
| 2008/0308109 A1 | 12/2008 | Brain |
| 2008/0312954 A1 | 12/2008 | Ullrich et al. |
| 2008/0319513 A1 | 12/2008 | Pu et al. |
| 2009/0005651 A1 | 1/2009 | Ward et al. |
| 2009/0007909 A1 | 1/2009 | Carrico |
| 2009/0038921 A1 | 2/2009 | Kaps et al. |
| 2009/0054743 A1 | 2/2009 | Stewart |
| 2009/0055735 A1 | 2/2009 | Zaleski |
| 2009/0062674 A1 | 3/2009 | Jin |
| 2009/0062725 A1 | 3/2009 | Goebel |
| 2009/0063181 A1 | 3/2009 | Nho et al. |
| 2009/0065004 A1 | 3/2009 | Childers et al. |
| 2009/0076342 A1 | 3/2009 | Amurthur et al. |
| 2009/0124917 A1 | 5/2009 | Hatlestad et al. |
| 2009/0125333 A1 | 5/2009 | Heywood et al. |
| 2009/0126734 A1 | 5/2009 | Dunsmore et al. |
| 2009/0131758 A1 | 5/2009 | Heywood et al. |
| 2009/0133701 A1 | 5/2009 | Brain |
| 2009/0143694 A1 | 6/2009 | Krauss et al. |
| 2009/0145438 A1 | 6/2009 | Brain |
| 2009/0149200 A1 | 6/2009 | Jayasinghe et al. |
| 2009/0149723 A1 | 6/2009 | Krauss et al. |
| 2009/0149927 A1 | 6/2009 | Kneuer et al. |
| 2009/0150184 A1 | 6/2009 | Spahn |
| 2009/0159082 A1 | 6/2009 | Eger |
| 2009/0165795 A1 | 7/2009 | Nadjafizadeh et al. |
| 2009/0171167 A1 | 7/2009 | Baker, Jr. |
| 2009/0171176 A1 | 7/2009 | Andersohn |
| 2009/0192421 A1 | 7/2009 | Huster et al. |
| 2009/0205661 A1 | 8/2009 | Stephenson et al. |
| 2009/0205663 A1 | 8/2009 | Vandine et al. |
| 2009/0209828 A1 | 8/2009 | Musin |
| 2009/0209849 A1 | 8/2009 | Rowe et al. |
| 2009/0216145 A1 | 8/2009 | Skerl et al. |
| 2009/0221926 A1 | 9/2009 | Younes |
| 2009/0229611 A1 | 9/2009 | Martin |
| 2009/0240523 A1 | 9/2009 | Friedlander et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0244003 A1 | 10/2009 | Bonnat |
| 2009/0247891 A1 | 10/2009 | Wood |
| 2009/0250054 A1 | 10/2009 | Loncar et al. |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0004517 A1 | 1/2010 | Bryenton et al. |
| 2010/0011307 A1 | 1/2010 | Desfossez et al. |
| 2010/0022904 A1 | 1/2010 | Centen |
| 2010/0024820 A1 | 2/2010 | Bourdon |
| 2010/0030092 A1 | 2/2010 | Kristensen et al. |
| 2010/0048985 A1 | 2/2010 | Henke et al. |
| 2010/0048986 A1 | 2/2010 | Henke et al. |
| 2010/0049034 A1 | 2/2010 | Eck et al. |
| 2010/0049264 A1 | 2/2010 | Henke et al. |
| 2010/0049265 A1 | 2/2010 | Henke et al. |
| 2010/0051026 A1 | 3/2010 | Graboi |
| 2010/0051029 A1 | 3/2010 | Jafari et al. |
| 2010/0056852 A1 | 3/2010 | Henke et al. |
| 2010/0056853 A1 | 3/2010 | Henke et al. |
| 2010/0056855 A1 | 3/2010 | Henke et al. |
| 2010/0056929 A1 | 3/2010 | Stahmann et al. |
| 2010/0056941 A1 | 3/2010 | Henke et al. |
| 2010/0056942 A1 | 3/2010 | Henke et al. |
| 2010/0057148 A1 | 3/2010 | Henke et al. |
| 2010/0059061 A1 | 3/2010 | Brain |
| 2010/0063348 A1 | 3/2010 | Henke et al. |

(56) References Cited

U.S. PATENT DOCUMENTS

| | | |
|---|---|---|
| 2010/0063350 A1 | 3/2010 | Henke et al. |
| 2010/0063365 A1 | 3/2010 | Pisani et al. |
| 2010/0069761 A1 | 3/2010 | Karst et al. |
| 2010/0069774 A1 | 3/2010 | Bingham et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0072055 A1 | 3/2010 | Tanaka et al. |
| 2010/0076278 A1 | 3/2010 | van der Zande et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081890 A1 | 4/2010 | Li et al. |
| 2010/0081955 A1 | 4/2010 | Wood, Jr. et al. |
| 2010/0083968 A1 | 4/2010 | Wondka et al. |
| 2010/0095961 A1 | 4/2010 | Tornesel et al. |
| 2010/0130873 A1 | 5/2010 | Yuen et al. |
| 2010/0139660 A1 | 6/2010 | Adahan |
| 2010/0147303 A1 | 6/2010 | Jafari et al. |
| 2010/0160839 A1 | 6/2010 | Freeman et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0274100 A1 | 10/2010 | Behar et al. |
| 2010/0282259 A1 | 11/2010 | Figueiredo et al. |
| 2010/0288283 A1 | 11/2010 | Campbell et al. |
| 2010/0298718 A1 | 11/2010 | Gilham et al. |
| 2010/0300446 A1 | 12/2010 | Nicolazzi et al. |
| 2010/0312132 A1 | 12/2010 | Wood et al. |
| 2010/0317980 A1 | 12/2010 | Guglielmino |
| 2011/0004489 A1 | 1/2011 | Schoenberg et al. |
| 2011/0009746 A1 | 1/2011 | Tran et al. |
| 2011/0011400 A1 | 1/2011 | Gentner et al. |
| 2011/0015493 A1 | 1/2011 | Koschek |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandine et al. |
| 2011/0054289 A1 | 3/2011 | Derchak et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawfor, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0304995 A1 | 12/2012 | Kauc |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0025596 A1 | 1/2013 | Jafari et al. |
| 2013/0025597 A1 | 1/2013 | Doyle et al. |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |

FOREIGN PATENT DOCUMENTS

| | | |
|---|---|---|
| EP | 1464357 | 10/2004 |
| GB | 2319967 | 6/1998 |
| WO | WO 9014852 | 12/1990 |
| WO | WO 9308534 | 4/1993 |
| WO | WO 9312823 | 7/1993 |
| WO | WO 9314696 | 8/1993 |
| WO | WO 9414374 | 7/1994 |
| WO | WO 9508471 | 3/1995 |
| WO | WO 9532480 | 11/1995 |
| WO | WO 9624285 | 8/1996 |
| WO | WO 9720592 | 6/1997 |
| WO | WO 9811840 | 3/1998 |
| WO | WO 9814116 | 4/1998 |
| WO | WO 9829790 | 7/1998 |
| WO | WO 9833554 | 8/1998 |
| WO | WO 9840014 | 9/1998 |
| WO | WO 9841267 A1 | 9/1998 |
| WO | WO 9841267 C1 | 9/1998 |
| WO | WO 9841269 | 9/1998 |
| WO | WO 9841270 | 9/1998 |
| WO | WO 9841271 | 9/1998 |
| WO | WO 9858219 | 12/1998 |
| WO | WO 9903524 | 1/1999 |
| WO | WO 9952431 | 10/1999 |
| WO | WO 9952437 | 10/1999 |
| WO | WO 9959460 | 11/1999 |
| WO | WO 9962403 | 12/1999 |

(56) References Cited

FOREIGN PATENT DOCUMENTS

| | | |
|---|---|---|
| WO | WO 0018293 | 4/2000 |
| WO | WO 0019886 | 4/2000 |
| WO | WO 0062664 | 10/2000 |
| WO | WO 0100264 | 1/2001 |
| WO | WO 0100265 | 1/2001 |
| WO | WO 0128416 | 4/2001 |
| WO | WO 0134022 | 5/2001 |
| WO | WO 0245566 | 6/2002 |
| WO | WO 02082967 | 10/2002 |
| WO | WO 03015005 | 2/2003 |
| WO | WO 03024317 | 3/2003 |
| WO | WO 03045493 | 6/2003 |
| WO | WO 03053503 | 7/2003 |
| WO | WO 03060650 | 7/2003 |
| WO | WO 03060651 | 7/2003 |
| WO | WO 03075989 | 9/2003 |
| WO | WO 03075990 | 9/2003 |
| WO | WO 03075991 | 9/2003 |
| WO | WO 03084405 | 10/2003 |
| WO | WO 2004014216 | 2/2004 |
| WO | WO 2004014226 | 2/2004 |
| WO | WO 2004032719 | 4/2004 |
| WO | WO 2004043254 | 5/2004 |
| WO | WO 2005010796 | 2/2005 |
| WO | WO 2005024729 | 3/2005 |
| WO | WO 2005055825 | 6/2005 |
| WO | WO 2005056087 | 6/2005 |
| WO | WO 2005069740 | 8/2005 |
| WO | WO 2005077260 | 8/2005 |
| WO | WO 2005112739 | 12/2005 |
| WO | WO 2006008745 | 1/2006 |
| WO | WO 2006009830 | 1/2006 |
| WO | WO 2006037184 | 4/2006 |
| WO | WO 2006050388 | 5/2006 |
| WO | WO 2006051466 | 5/2006 |
| WO | WO 2006078432 | 7/2006 |
| WO | WO 2006094055 | 9/2006 |
| WO | WO 2006096080 | 9/2006 |
| WO | WO 2006109072 | 10/2006 |
| WO | WO 2006123956 | 11/2006 |
| WO | WO 2006125986 | 11/2006 |
| WO | WO 2006125987 | 11/2006 |
| WO | WO 2006125989 | 11/2006 |
| WO | WO 2006125990 | 11/2006 |
| WO | WO 2006137067 | 12/2006 |
| WO | WO 2007033050 | 3/2007 |
| WO | WO 2007106804 | 9/2007 |
| WO | WO 2007145948 | 12/2007 |
| WO | WO 2008030091 | 3/2008 |
| WO | WO 2008042699 | 4/2008 |
| WO | WO 2008058997 | 5/2008 |
| WO | WO 2008062554 | 5/2008 |
| WO | WO 2008113410 | 9/2008 |
| WO | WO 2008118951 | 10/2008 |
| WO | WO 2008140528 | 11/2008 |
| WO | WO 2008146264 | 12/2008 |
| WO | WO 2008148134 | 12/2008 |
| WO | WO 2009024967 | 2/2009 |
| WO | WO 2009027864 | 3/2009 |
| WO | WO 2009036334 | 3/2009 |
| WO | WO 2009124297 | 10/2009 |
| WO | WO 2010009531 | 1/2010 |
| WO | WO 2010020980 | 2/2010 |
| WO | WO 2010021730 | 2/2010 |
| WO | WO 2010039989 | 4/2010 |
| WO | WO 2010126916 | 11/2010 |
| WO | WO 2010141415 | 12/2010 |
| WO | WO 2011005953 | 1/2011 |
| WO | WO 2011022242 | 2/2011 |

OTHER PUBLICATIONS

7200 Ventilatory System: Addendum/Errata. Nellcor Puritan Bennett, Part No. 4-023576-00, Rev. A, Apr. 1988, pp. 1-32.
800 Operator's and Technical Reference Manual. Series Ventilator System, Nellcor Puritan Bennett, Part No. 4-070088-00, Rev. L, Aug. 2010, pp. 1-476.
840 Operator's and Technical Reference Manual. Ventilator System, Nellcor Puritan Bennett, Part No. 4-075609-00, Rev. G, Oct. 2006, pp. 1-424.
Non-Final Office Action mailed Jan. 28, 2010, in U.S. Appl. No. 11/408,457.
Non-Final Office Action mailed Jun. 9, 2010, in U.S. Appl. No. 11/408,457.
Final Office Action mailed Dec. 8, 2010, in U.S. Appl. No. 11/408,457.
Cabello and Mancebo, Work of breathing, Intensive Care Med (2006) 32:1311-1314.
MA Banner, RR Kirby, A Gabrielli, PB Blanch, AJ Layon. Partially and Totally Unloading Respiratory Muscles Based on Real-Time Measurements of Work of Breathing: A Clinical Approach; Chest 1994; 106; 1835-1842.
Notice of Allowance mailed Jun. 21, 2011, in Application U.S. Appl. No. 11/408,457, 8 pgs.
U.S. Appl. 13/543,574, Office Action mailed Mar. 18, 2013, 24 pgs.
U.S. Appl. No. 13/543,574, Office Action mailed Oct. 7, 2013, 13 pgs.
US 7,284,551, 10/2007, Jones et al. (withdrawn)

* cited by examiner

WORK OF BREATHING DISPLAY FOR A VENTILATION SYSTEM

RELATED APPLICATIONS

This application is a continuation of prior application Ser. No. 11/408,457, filed Apr. 21, 2006, now U.S. Pat. No. 8,021,310, and entitled "WORK OF BREATHING DISPLAY FOR A VENTILATION SYSTEM," which application is hereby incorporated herein by reference.

INTRODUCTION

One indication of a patient's condition during respiration support is the status of the patient's work of breathing (WOB). Work of breathing may be defined as the work associated with inflating the patient's lungs during a breathing cycle. During respiration support, a ventilator provides at least a portion of the total work of breathing for the patient. The total work of breathing ($WOB_{TOTAL}$) may generally be defined as the sum of the work of breathing provided by the patient ($WOB_{PATIENT}$) and the work of breathing support provided by the ventilator ($WOB_{VENTILATOR}$).

The work of breathing provided by the patient ($WOB_{PATIENT}$) may be approximated as the sum of two components: an elastic WOB component ($WOB_{PATIENT\text{-}ELASTIC}$) and a resistive WOB component ($WOB_{PATIENT\text{-}RESISTIVE}$). The elastic WOB component is generally defined as the work required to overcome the elastance of the patient's respiratory system, while the resistive component is generally defined as the work required to overcome the airway resistance of the patient's respiratory system.

Elastance may generally be defined in terms of the elastic properties of the lung and chest, or the forces associated with expanding the lung. In particular, the degree of stiffness of the lung-chest region may be referred to as the elastance of the respiratory system. The elastance of the respiratory system may also be discussed in terms of compliance, which may be defined as the inverse of elastance. Generally, the easier it is to stretch the lung-chest region.

Resistance forces, or the non-elastic forces at work in the breathing cycle, are the forces associated with moving air through a patient's airways. Lung resistance may be at least partially defined by a patient's physiological conditions. For example, patients suffering from asthma typically experience muscular constriction of the bronchi. Such patients may also experience swelling of the bronchial mucosa. The work required to achieve a particular amount of air flow through the breathing passageways generally increases in proportion to the severity of constriction. In some ventilation systems, flow and pressure sensors are used to compute estimates of the patient's resistance and compliance.

One or more WOB values, e.g., the total WOB, the patient's WOB (WOB PATIENT), the ventilator's WOB (WOB VENTILATOR), the elastic WOB component (WOB PATIENT-ELASTIC), and/or the resistive WOB component (WOB PATIENT-RESISTIVE) may be determined and/or monitored in various manners. For example, a patient's WOB may be determined from either measured or estimated values relating to the patient's respiratory physiology by applying direct or indirect approaches and following established algorithms. Measured values may be obtained more directly by invasive procedures, e.g., procedures that require the installation of an esophageal balloon. Such techniques are typically invasive and require specialized skill. Thus, outside of the research setting it may be undesirable to obtain WOB measures employing such invasive means.

In a pressure assisted ventilation (PAV) system, the patient's work of breathing ($WOB_{PATIENT}$), the elastic WOB component ($WOB_{PATIENT\text{-}ELASTIC}$), and/or the resistive WOB component ($WOB_{PATIENT\text{-}RESISTIVE}$) may be estimated by inputting measurements from various sensors into the breathing algorithms. In PAV ventilation, the patient is supplied with continuous pressure assistance throughout an inspiratory effort and in direct proportion to the moment-to-moment inspiratory effort. Typically, none of the instantaneous inspiratory pressure, the instantaneous flow, or the resulting volume are set by the caregiver. Because the PAV breathing algorithm harmoniously links the ventilator to the patient, the patient effectively "drives" the ventilator. By appropriately setting the value of the proportionality (% support) control, the caregiver may effectively partition the total WOB between the patient ($WOB_{PATIENT}$) and the ventilator ($WOB_{VENTILATOR}$).

The values of the patient's lung-chest compliance and lung resistance may be continuously estimated and inserted into the PAV breathing algorithm in order for the algorithm to function properly. These estimates may be made automatically by the ventilator and fed back to the breathing algorithm as perhaps better fits the needs of the patient in intensive care, whereas manual techniques may be used to estimate the values for more stable patients, e.g., in a home setting.

WORK OF BREATHING DISPLAY FOR A VENTILATION SYSTEM

In accordance with the present disclosure, systems and methods for monitoring and/or displaying one or more work of breathing measures are provided.

According to one embodiment, a breathing support system is provided. The system may include a breathing support device configured to deliver gas to a patient, a software-generated work of breathing graphic indicating one or more work of breathing measures regarding the patient's breathing, and a display device associated with the breathing support device, the display device configured to display the software-generated graphic. The software-generated graphic includes a scale and one or more work of breathing indicators that move relative to the scale.

According to one embodiment, a breathing support system is provided. The system may include a breathing support device configured to deliver gas to a patient, a software-generated work of breathing graphic indicating one or more work of breathing measures regarding the patient's breathing, and a display device associated with the breathing support device, the display device configured to display the software-generated graphic. The software-generated graphic includes an elastic-resistive work of breathing graphic including a first portion and a second portion, the first portion indicating a measure of an elastic work of breathing component and the second portion indicating a measure of a resistive work of breathing component. The relative sizes of the first and second portions of the elastic-resistive work of breathing graphic dynamically adjust on a bar to indicate the measure of the elastic work of breathing component relative to the measure of the resistive work of breathing component.

These and various other features as well as advantages will be apparent from a reading of the following detailed description and a review of the associated drawings. Additional features are set forth in the description that follows and, in part, will be apparent from the description, or may be learned by practice of the described embodiments. The benefits and features will be realized and attained by the structure particularly pointed out in the written description and claims hereof as well as the appended drawings.

It is to be understood that both the foregoing general description and the following detailed description are exemplary and explanatory and are intended to provide further explanation of the claimed invention.

BRIEF DESCRIPTION OF THE DRAWINGS

The following drawing figures, which form a part of this application, are illustrative of embodiments systems and methods described below and are not meant to limit the scope of the invention in any manner, which scope shall be based on the claims appended hereto.

DETAILED DESCRIPTION

Figure 1:
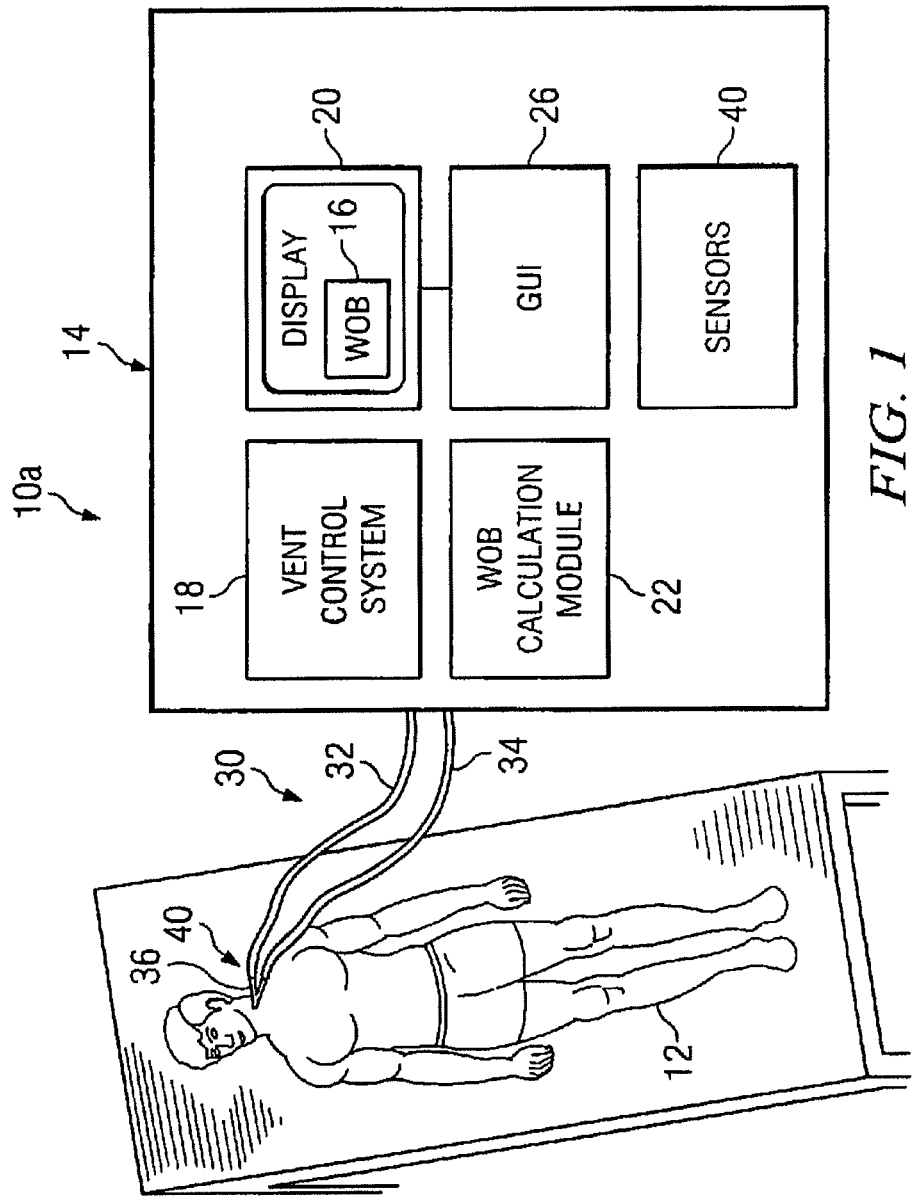
FIG. 1 illustrates a ventilation system for providing ventilation support to a patient, including a ventilator configured to display a work of breathing graphic, according to one embodiment of the disclosure.

Selected embodiments of the disclosure may be understood by reference, in part, to FIGS. 1-9, wherein like numbers refer to same and like parts.

In general, the present disclosure describes generating and/or displaying a work of breathing graphic (WOB graphic) for use with a ventilator or other breath delivery or breathing support system that may provide caregivers with various information concerning work of breathing through an easily understood graphical display. The WOB graphic may be used, e.g., for monitoring and/or adjusting the amount of work of breathing contributed by the patient and/or the amount contributed by the ventilator. For example, the display may allow a caregiver to monitor a patient's work of breathing in real time or substantially in real time. A caregiver may use such information for various purposes, such as, for example, to ensure that the patient's work of breathing is within a safe or desirable range and/or to determine whether and/or how to adjust one or more ventilator settings (e.g., to increase or decrease respiratory support to the patient).

In some embodiments, the WOB graphic may depict (graphically, numerically, or otherwise) the effect that changes in one or more ventilator settings have on the work of breathing being contributed by a patient, e.g., in order to determine whether or not such adjustments are causing a patient to work at a level above, within, or below an acceptable or desired range of work. The WOB graphic may be user-friendly such that caregivers of various degrees of technical sophistication may understand or interpret the display and/or be able to utilize the display for implementing or managing a respiration support strategy. Additionally, the WOB graphic may be used in conjunction with traditional ventilation systems and applications, e.g., pressure assisted ventilation (PAV) applications.

The WOB graphic may be displayed via any of a variety of media. For example, in some embodiments, the WOB graphic may be displayed by a ventilator or a ventilator control system. In other embodiments, the WOB graphic may be displayed on a separate display device (e.g., separate from a ventilator). In particular embodiments, the WOB graphic may be displayed in association with a ventilation control system for administering a respiration support strategy. In such embodiments, a ventilator may be connected to a graphic user interface having a digital processor, a display screen, and/or one or more user inputs, or the ventilator may itself include a graphic user interface. These components may cooperate to assist a caregiver in setting up and/or adjusting the work of breathing being provided by a patient and/or the work of breathing being provided by the ventilator.

In some embodiments, the WOB graphic may indicate the total work of breathing ($WOB_{TOTAL}$), the patient's work of breathing ($WOB_{PATIENT}$) (neither of which, one of which, or both of which advance or retreat along a scale) and/or the components of the patient's WOB—an elastic WOB component ($WOB_{PATIENT-ELASTIC}$) and a resistive WOB component ($WOB_{PATIENT-RESISTIVE}$). For example, the WOB graphic may include a $WOB_{TOTAL}$ graphic or indicator that indicates the total work of breathing, a $WOB_{PATIENT}$ graphic or indicator that indicates the patient's work of breathing, and an elastic-resistive WOB graphic that indicates a measure of the elastic WOB component ($WOB_{PATIENT-ELASTIC}$) relative to a measure of the resistive WOB component ($WOB_{PATIENT-RESISTIVE}$). As another example, the WOB graphic may include a $WOB_{TOTAL}$ graphic or indicator that indicates the total work of breathing, a $WOB_{PATIENT}$ graphic or indicator that indicates the patient's work of breathing, an elastic WOB graphic that indicates a measure of the elastic WOB component ($WOB_{PATIENT-ELASTIC}$), and a resistive WOB graphic that indicates a measure of the resistive WOB component ($WOB_{PATIENT-RESISTIVE}$). In other embodiments, one or more additional and/or other components of a total work of breathing measure may be displayed, e.g., the ventilator work of breathing ($WOB_{VENTILATOR}$).

In some embodiments, the WOB graphic may include a scale having any suitable shape and configuration (e.g., a linear scale, a circular or semicircular scale, or an elliptical scale) and one or more indicators that move relative to the scale to indicate one or more work of breathing parameters. For example, the WOB graphic may include a first indicator that moves relative to the scale to represent a measure of $WOB_{TOTAL}$, and a second indicator that moves relative to the scale to represent a measure of $WOB_{PATIENT}$. The scale may be divided into sectors that generally correspond to different work of breathing levels. The sectors may be visibly discernable from each other (or at least from immediately adjacent sectors). For example, the sectors may be color-coded or distinctively shaded.

An elastic-resistive WOB graphic may be divided into a first portion and a second portion, the first portion indicating the elastic WOB component ($WOB_{PATIENT-ELASTIC}$) and the second portion indicating the resistive WOB component ($WOB_{PATIENT-RESISTIVE}$). The relative sizes of the first and second portions of the elastic-resistive WOB graphic may dynamically adjust to indicate the measure of the elastic WOB component relative to the measure of the resistive WOB component. In certain embodiments, the overall size of the elastic-resistive WOB graphic remains constant as the relative sizes of the first and second portions dynamically adjust.

Figure 2:
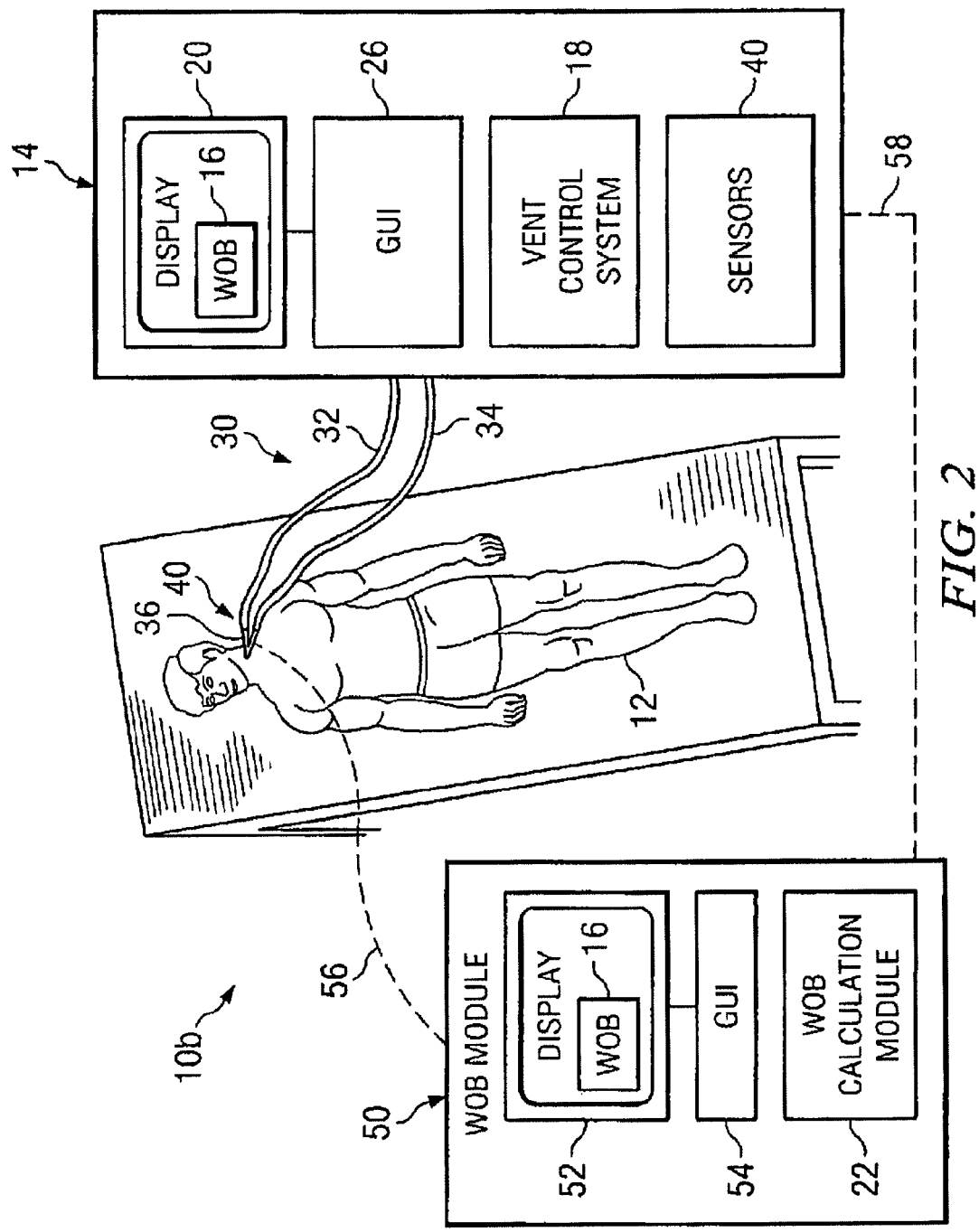
FIG. 2 illustrates a ventilation system for providing ventilation support to a patient, including a ventilator and a separate module for displaying a work of breathing graphic, according to one embodiment of the disclosure.

FIGS. 1 and 2 illustrate two example embodiments of a ventilation system including a displayed WOB graphic. More particularly, FIG. 1 illustrates an example ventilation system including a ventilator configured to display a work of breathing graphic, while FIG. 2 illustrates an example ventilation system including a ventilator and a separate module for displaying a work of breathing graphic.

Referring to FIG. 1, a ventilation system 10a for providing breathing assistance to a patient 12 may include a ventilator 14 configured to display a WOB graphic 16 and one or more devices for connecting ventilator 14 to patient 12. As used throughout this document, the term "ventilator" may refer to any device, apparatus, or system for delivering breathing gas to a patient, e.g., a ventilator, a respirator, a CPAP device, or a BiPAP device. The term "patient" may refer to any person who is receiving breathing support from a ventilation system, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, etc.

Ventilator 14 may include a ventilation control system 18, a display device 20, and a WOB calculation module 22. Ventilation control system 18 may be operable to control the ventilation support provided by ventilator 14 based on various inputs, such as inputs received from an operator and/or data received from various sensors, as discussed below. Display device 20 may be fully or partially integrated with ventilator 14 and may comprise, e.g., a touch screen display or other visual display. Display device 20 may be configured to display various information regarding the ventilation of patient 12, including WOB graphic 16 and/or other information regarding the ventilation of patient 12 (e.g., tidal volume, minute ventilation, and respiration rate). WOB graphic 16 may display one or more work of breathing measures in any suitable manner, e.g., graphically, numerically, or otherwise. WOB graphic 16 may be a full screen display or may occupy a portion of a display screen. For example, WOB graphic 16 may be located in a window or a portion of a display that includes other information regarding the ventilation of patient 12.

Display device 20 may be part of or otherwise associated with, a graphic user interface 26. In this embodiment, graphic user interface 26 may be configured to display WOB graphic 16 and/or other information via display device 20 and/or provide an interface for accepting input from human operators via display device 20 and/or other input devices (e.g., to set or modify ventilation settings, to access data, and/or to change or configure the display).

Patient 12 may be connected to ventilator 14 by a breathing circuit 30 that may include an inspiration conduit 32, an exhalation conduit 34, and/or a patient connection apparatus 36. Patient connection apparatus 36 may include any device or devices configured to connect breathing circuit 30 to one or more breathing passageways of patient 12. For example, patient connection apparatus 36 may include a patient connection tube directly connected to the patient's trachea, an artificial airway (e.g., an endotracheal tube or other device) inserted in the patient's trachea, and/or a mask or nasal pillows positioned over the patient's nose and/or mouth. In embodiments including a patient connection tube, the patient connection tube may include a Wye (or "Y") connector.

Ventilation system 10a may include one or more sensors 40 for sensing, detecting, and/or monitoring one or more parameters related to the ventilation of patient 12, e.g., parameters regarding the ventilation provided by ventilator 14 and/or physiological parameters regarding patient 12. For example, sensors 40 may include one or more devices for measuring various parameters of gas flowing into or out of patient 12 or ventilator 14, e.g., the pressure, flow rate, flow volume, temperature, gas content, and/or humidity of such gas flow. Thus, sensors 40 may include, e.g., one or more pressure sensors, flow meters, transducers, and/or oxygen sensors. Sensors 40 may be located at one or more various locations in ventilation system 10 for monitoring the pressure and or flow of gasses flowing into and/or out of patient 12 and/or ventilator 14. For example, one or more sensors 40 may be located in or proximate ventilator 14, breathing circuit 30, and/or patient connection apparatus 36. For example, depending on the particular embodiment, one or more sensors 40 may be located within or proximate to ventilator 14, inspiration conduit 32 and/or exhalation conduit 34 or breathing circuit 30, an artificial airway, and/or a Wye connector.

As discussed above, ventilation control system 18 may be operable to control the ventilation support provided by ventilator 14 based on various input received from an operator (e.g., via graphic user interface 26 and/or other user interfaces on ventilator 14) and/or data received from one or more sensors 40. For example, ventilation control system 18 may regulate the pressure and/or flow of gas delivered to a patient based at least on data received from sensors 40.

WOB calculation module 22 may be operable to calculate or otherwise determine one or more work of breathing measures based on various input data, including data collected by sensors 40, as described in greater detail below with reference to FIG. 3. Such work of breathing measures determined by WOB calculation module 22 may then be communicated to graphic user interface 26 for display via display device 20.

According to the embodiment shown in FIG. 2, a ventilation system 10b for providing breathing assistance to a patient 12 may include a ventilator 14, one or more devices for connecting ventilator 14 to patient 12, and a separate WOB module 50. Ventilator 14 may include a ventilation control system 18 and a display screen 20, such as discussed above regarding the embodiment shown in FIG. 1. Ventilation control system 18 may be operable to control the ventilation support provided by ventilator 14 based on various inputs, such as inputs received from an operator and/or data received from various sensors, as discussed below. Display device 20 may be fully or partially integrated with ventilator 14 and may comprise, e.g., a touch screen display or other visual display. Display device 20 may be configured to display various information regarding the ventilation of patient 12. Display device 20 may be part of or otherwise associated with, a graphic user interface 26. In this embodiment, graphic user interface 26 may be configured to display various information via display device 20 and/or provide an interface for accepting input from human operators via display device 20 and/or other input devices (e.g., to set or modify ventilation settings, to access data, and/or to change or configure the display).

WOB module 50 may include a display device 52, a WOB calculation module 22, and any other suitable hardware or software for determining and/or displaying one or more WOB measures. For example, WOB module 50 may be configured to display a WOB graphic 16 via display device 52, e.g., a touch screen display or other visual display. As discussed above, WOB graphic 16 may be a full screen display or may occupy a portion of a display screen. In some embodiments, WOB module 50 may include a graphic user interface 54, which may be operable to display WOB graphic 16 and/or other information via display device 52 and, in some embodiments, provide an interface for accepting input from human operators via display device 52 and/or other user input devices (e.g., to set or modify various settings, access data, and/or change or configure the display).

WOB calculation module 22 may be operable to calculate or otherwise determine one or more work of breathing measures based on various input data, including data collected by sensors 40. WOB calculation module 22 may receive such input data from any suitable component of ventilation system 10b. For example, WOB module 50 may be communicatively coupled to one or more sensors 40 (e.g., sensors 40 located at or proximate to an artificial airway (e.g., an endotracheal tube or other device), a Wye connector, or breathing circuit 30) such that WOB module 50 may receive data directly from such sensors 40, e.g., as indicated by dashed line 56. Alternatively, WOB module 50 may be communicatively coupled to ventilator 14 such that WOB module 50 may receive data from ventilator 14 (e.g., as indicated by dashed line 58), which may include data received from various sensors 40 (which data may or may not be first processed or otherwise acted on by ventilator 14 and then communicated to WOB module 50). WOB calculation module 22 may receive data from sensors 40 directly or indirectly in any other suitable manner. WOB calculation module 22 may then calculate or otherwise determine one or more work of breathing measures based on such data from sensors 40, and communicate the determined work of breathing measures for display via display device 52.

It should be understood that components of ventilation systems 10a and 10b may include any hardware, software, firmware or other components suitable for providing ventilation assistance to patient 12 and/or determining and displaying one or more work of breathing measures. For example, ventilator 14 may include various processors, memory devices, user inputs, status indicators, audio devices, and/or software or other logic for providing various ventilator functions.

Figure 3:
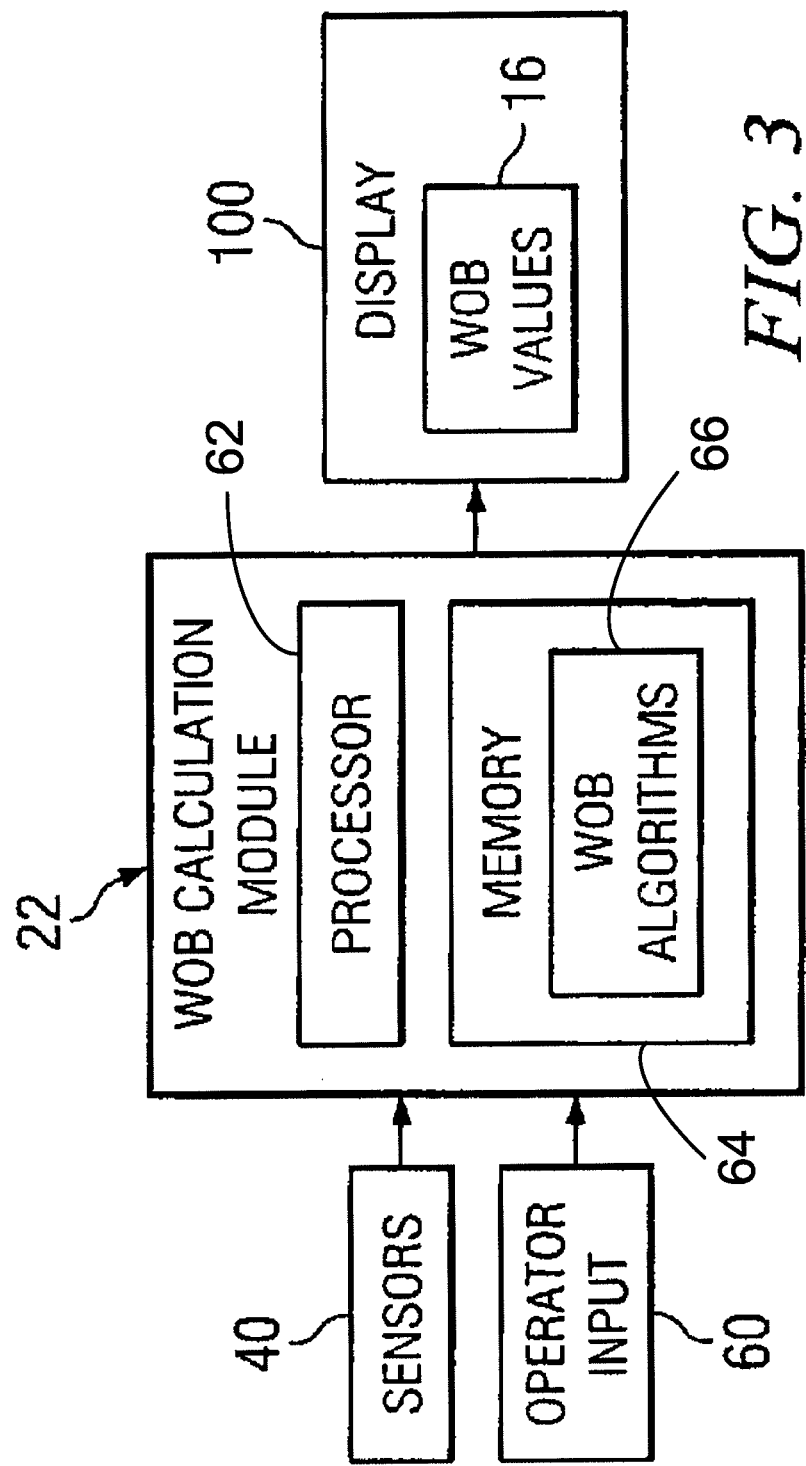
FIG. 3 is a block diagram illustrating an example system for determining and displaying work of breathing measures, according to some embodiments.

FIG. 3 is a block diagram illustrating an example system for determining and displaying work of breathing measures, according to some embodiments. As discussed above, WOB calculation module 22 may be operable to calculate or otherwise determine one or more work of breathing measures based on various input data. Such input data may include data received from sensors 40 and/or data or settings input by an operator, indicated in FIG. 3 as operator input 60. Such WOB measures may then be represented in a WOB graphic 16 displayed on any suitable display device 100, e.g., display devices 20 or 52 discussed above with reference to FIGS. 1 and 2. For example, WOB calculation module 22 may calculate measures for $WOB_{TOTAL}$, $WOB_{PATIENT}$, $WOB_{VENTILATOR}$, $WOB_{PATIENT-ELASTIC}$, and/or $WOB_{PATIENT-RESISTIVE}$. One, some, or all of these measures may then be displayed in a WOB graphic 16 in any suitable manner, e.g., using graphic and/or numeric representations.

WOB calculation module 22 may include a processor 62, memory 64, and any other suitable hardware or software. Memory 64 may store one or more WOB algorithms 66 and/or any other suitable software or logic that may be executable by processor 62 for calculating one or more work of breathing measures, e.g., as discussed below.

WOB calculation module 22 may use data collected by sensors 40 to calculate or otherwise determine work of breathing measures in any of a variety of manners. For example, in some embodiments in which a balloon is inserted in the patient's esophagus, sensors 40 may be used to monitor pressure and volume (flow*time) at the airway opening (e.g., at or proximate to a Wye connector). Such data may be communicated to WOB calculation module 22, which may determine or calculate one or more WOB measures based on such received data.

Alternatively, WOB calculation module 22 may calculate estimated WOB measures based on data monitored entirely external to the patient, e.g., using WOB 66 algorithms that use data from sensors 40 as inputs. For example, in a pressure assisted ventilation (PAV) environment, WOB calculation module 22 may receive data from sensors 40 positioned in or proximate to ventilator 14 and calculate estimated WOB measures using such data as inputs for one or more suitable PAV algorithms. Example techniques for providing or generating PAV, which may lead to WOB calculations, are disclosed in U.S. Pat. No. 5,107,830, which is hereby incorporated by reference in its entirety. In addition, example techniques for determining or approximating resistance and/or elastance in a PAV environment, which may be used in calculating WOB values, are disclosed in U.S. Pat. No. 5,884,622 and U.S. Pat. No. 6,837,242, which are hereby incorporated by reference in their entirety.

Thus, in some embodiments, WOB calculation module 22 may include or use such techniques and/or other known techniques for calculating estimated WOB measures, which may then be displayed via WOB graphic 16. It should be understood that WOB measures may be measured, estimated, or otherwise determined in any other suitable manner in both PAV and non-PAV environments.

Various example embodiments of WOB graphic 16 are illustrated in FIGS. 4-9, as discussed in greater detail below. WOB graphic 16 may be displayed on any suitable display device 100, e.g., display devices 20 or 52 discussed above with reference to FIGS. 1 and 2. Although the present disclosure discusses the generation and/or display of a WOB graphic in connection with a ventilator, it should be understood that the disclosed WOB graphics may similarly be used in connection with other stand-alone systems or devices that calculate WOB measures.

WOB graphic 16 may comprise, e.g., a graphic on a general-purpose display screen or on a dedicated display or display device, and may be configured to provide a user-friendly display that represents a patient's work of breathing. However, display device 100 may additionally or alternatively be operable to visually represent patient data, alarm conditions, various charts, graphs, tables, and/or other such information as may be appropriate or useful to a caregiver in assessing a patient's respiratory or other vital functions. For example, the display of display device 100 may be divided into multiple sections, with one section displaying the WOB graphic 16 while one or more other sections display various other items such as ventilator parameters, patient data, etc. However, such information may alternatively be displayed in a non-sectored layout, e.g., intermingled or integrated with the WOB graphic 16.

As discussed above, WOB graphic 16 may indicate the total work of breathing ($WOB_{TOTAL}$), the patient's work of breathing ($WOB_{PATIENT}$), and/or the components of the patient's WOB—an elastic WOB component ($WOB_{PATIENT-ELASTIC}$) and a resistive WOB component ($WOB_{PATIENT-RESISTIVE}$). In some embodiments, WOB graphic 16 may include a scale having any suitable shape or configuration (e.g., a linear scale, a circular or semicircular scale, or an elliptical scale) and one or more indicators that move relative to the scale to indicate one or more work of breathing parameters.

For example, WOB graphic 16 may include a $WOB_{TOTAL}$ indicator that moves relative to the scale to represent a measure of $WOB_{TOTAL}$, and a $WOB_{PATIENT}$ indicator that moves relative to the scale to represent a measure of $WOB_{PATIENT}$. The scale may be divided into sectors that generally correspond to different work of breathing levels. The sectors may be visibly discernable from each other (or at least from immediately adjacent sectors).

The elastic-resistive WOB graphic may be divided into a first portion and a second portion, the first portion indicating the elastic WOB component ($WOB_{PATIENT-ELASTIC}$) and the second portion indicating the resistive WOB component ($WOB_{PATIENT-RESISTIVE}$). The overall size of the elastic-resistive WOB graphic may remain constant as the relative sizes of the first and second portions dynamically adjust to indicate a measure of the elastic WOB component relative to a measure of the resistive WOB component.

Each work of breathing measure (e.g., $WOB_{TOTAL}$, $WOB_{PATIENT}$, $WOB_{VENTILATOR}$, $WOB_{PATIENT-ELASTIC}$, and/or $WOB_{PATIENT-RESISTIVE}$) may be calculated and/or displayed using any suitable units or other parameter. For example, each WOB measure may be calculated and/or displayed as Joules (J), Joules per liter (J/L), Joules per minute (J/min) (i.e., power), or Joules per liter per kilogram (J/L/kg) (i.e., normalized power). Thus, it should be understood that the following discussion of WOB measures displayed in J/L is exemplary only.

Figure 4:
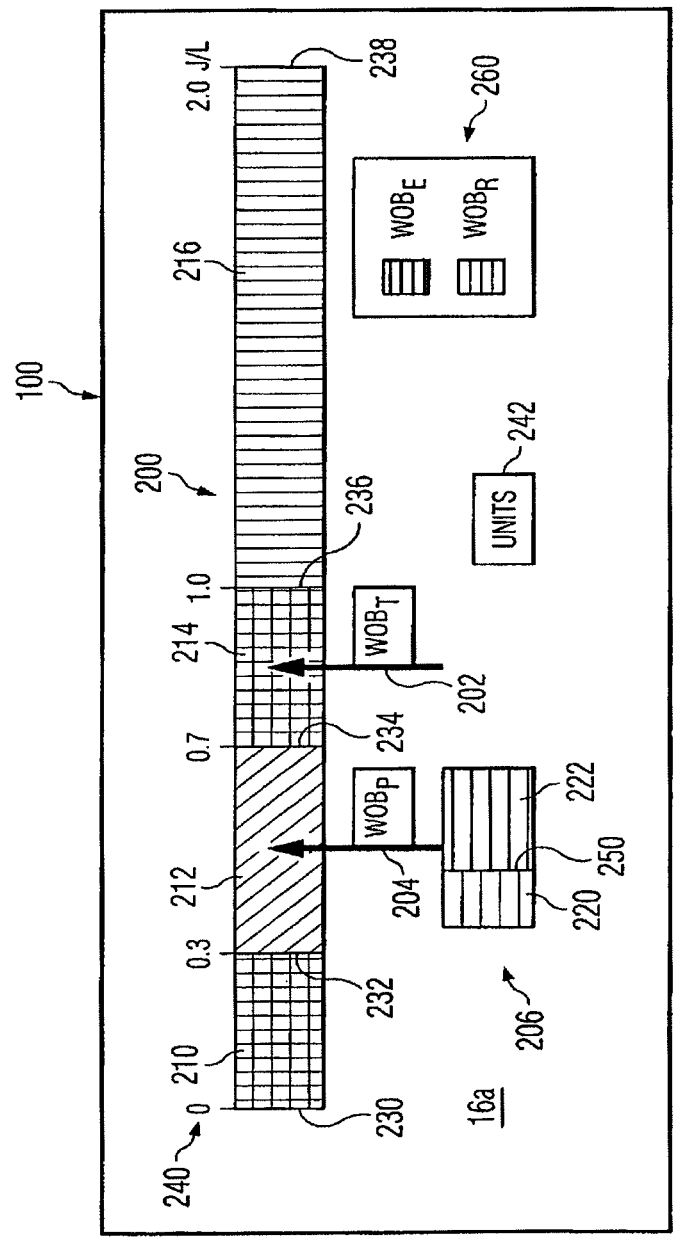
FIG. 4 illustrates a first example graphic work of breathing graphic, according to one embodiment of the disclosure.

FIG. 4 illustrates an example of a WOB graphic 16 a on a display device 100, according to one embodiment of the disclosure. WOB graphic 16 a may include a scale 200, a $WOB_{TOTAL}$ indicator 202 for indicating a measure of the total WOB, a $WOB_{PATIENT}$ indicator 204 for indicating a measure of the patient's WOB, and/or an elastic-resistive WOB indicator 206 for indicating the elastic and resistive WOB components of the patient's WOB. Scale 200 may be divided into a plurality of sectors that may generally correspond to different levels of acceptability, desirability, or safety regarding the patient's breathing. For example, such sectors may include at least one first sector representing a sub-normal work of breathing range, at least one second sector representing a normal work of breathing range, and at least one third sector representing a supra-normal work of breathing range. As another example, such sectors may include at least one first sector representing a sub-normal work of breathing range, at least one second sector representing a normal work of breathing range, at least one third sector representing a supra-normal work of breathing range, and at least one fourth sector representing a cautionary supra-normal work of breathing range.

In the example shown in FIG. 4, scale 200 may include four sectors, 210, 212, 214, and 216, which correspond to a sub-normal work of breathing range (sector 210), a normal work of breathing range (sector 212), a supra-normal work of breathing range (sector 214), and a cautionary supra-normal work of breathing range (sector 216). Sub-normal sector 210 may represent a range in which the patient's WOB may be below an appropriate level for administering a proper respiratory management protocol. Normal sector 212 may represent a range in which the patient's contributed WOB may be within an appropriate level for administering a proper respiratory management protocol. Supra-normal sector 214 may represent a range in which the patient's WOB may be above an appropriate level for administering a proper respiratory management protocol. Cautionary supra-normal sector 216 may represent a range in which the patient's WOB may be at a potentially harmful level. It should be understood that in other embodiments, WOB graphic 16 a may include any number and/or type(s) of sectors corresponding to any various conditions.

$WOB_{TOTAL}$ indicator 202 may comprise any pointer or other graphic that may advance and retreat along scale 200 as the $WOB_{TOTAL}$ changes over time (e.g., when a "percent support" setting is adjusted in a PAV ventilation environment). $WOB_{TOTAL}$ indicator 202 may include any suitable label or other identifier. In some embodiments, $WOB_{TOTAL}$ indicator 202 may include a numerical indication of the current $WOB_{TOTAL}$ measure. In other embodiments, no such numerical indication is displayed.

Similarly, $WOB_{PATIENT}$ indicator 204 may comprise any pointer or other graphic that may advance and retreat along scale 200 as the $WOB_{PATIENT}$ changes over time. $WOB_{PATIENT}$ indicator 204 may include any suitable label or other identifier. In some embodiments, $WOB_{PATIENT}$ indicator 204 may include a numerical indication of the current $WOB_{PATIENT}$ measure. In other embodiments, no such numerical indication is displayed.

Elastic-resistive WOB indicator 206 may be divided into a first indicator portion 220 representing a measure of $WOB_{PATIENT-ELASTIC}$, and a second indicator portion 222 representing a measure of $WOB_{PATIENT-RESISTIVE}$. The relative sizes of first and second indicator portions 220 and 222 may adjust dynamically as the relative measures of $WOB_{PATIENT-ELASTIC}$ and $WOB_{PATIENT-RESISTIVE}$ change over time. In some embodiments (e.g., as such as shown in FIG. 4), elastic-resistive WOB indicator 206 may be coupled to or otherwise associated with $WOB_{PATIENT}$ indicator 202, such that elastic-resistive WOB indicator 206 advances and retreats along scale 200 in coordination with $WOB_{PATIENT}$ indicator 202.

In this embodiment, scale 200 is oriented horizontally and $WOB_{TOTAL}$ indicator 202, $WOB_{PATIENT}$ indicator 204, and elastic-resistive WOB indicator 206 move horizontally along scale 200. In other embodiments, scale 200 may be oriented, and indicators 202, 204, and/or 206 may move, in any other direction (e.g., vertically, diagonally, in a stepped manner, or in a curved manner). Indicators 202, 204, and/or 206 may be positioned relative to scale 200 in any suitable manner. For example, 202, 204, and/or 206 may be positioned on the same side of scale 200 or on opposite sides of scale 200. As another example, one or more of indicators 202, 204, and/or 206 may be partially or fully superimposed over scale 200 and may advance or retreat along or through sectors 210-216 to indicate one or more work of breathing measures. Further, scale 200 and indicators 202, 204, and/or 206 may be positioned anywhere on WOB graphic 16 a.

In some embodiments, sector transition lines may divide the respective sectors of WOB scale 200. For example, as shown in FIG. 4, sector transition lines 230, 232, 234, 236, and 238 may divide sectors 210-216. Sector transition lines 230-238 may have any suitable shape and orientation. For example, sector transition lines 230-238 may be shaped to mirror or correspond to the shape or form of one or both ends of elastic-resistive WOB indicator 206. In other embodiments, scale 200 may not include sector transition lines.

In some embodiments, sectors 210-216 may be visibly discernable from each other, or at least from immediately adjacent sectors. For example, sectors 210-216 may be color-coded, shaded, or differently shaped such that sectors 210-216 may be visibly distinguishable from each other. Such color coding is represented in FIG. 4 by different levels of shading.

In an example embodiment, sector 210 may be color-coded yellow, sector 92 may be color-coded green, sector 94 may be color-coded yellow, and sector 96 may be color-coded orange, which may be commensurate with good human factors. It should be understood that any coloring may be chosen for each respective sector. Such color-coding may permit the caregiver to quickly and easily determine the location of indicators 202, 204, and/or 206 along the scale and/or provide the caregiver a quick indication of the status of the ventilatory support. In other embodiments, one, some or all of sectors 210-216 may be free from color-coding or other types of fill.

Elastic-resistive WOB indicator 206 may have any suitable shape and/or configuration. For example, elastic-resistive WOB indicator 206 may comprise a box, as shown in FIG. 4, or may take the form of a bar graph, a vertically-oriented line segment, or any other suitable symbol or graphic representation that may advance and retreat along sectors 210-216 to indicate measures of $WOB_{PATIENT-ELASTIC}$ and/or $WOB_{PATIENT-RESISTIVE}$. For example, in one embodiment, elastic-resistive WOB indicator 206 comprises a bar or other graphic that expands in length along scale 200 to indicate a measure of $WOB_{PATIENT}$. The bar or other graphic may be divided into indicator portions 220 and 222 that may adjust dynamically to indicate measures of $WOB_{PATIENT-ELASTIC}$ and $WOB_{PATIENT-RESISTIVE}$ over time. In some embodiments (e.g., where elastic-resistive WOB indicator 206 is superimposed over scale 200), the height of elastic-resistive WOB indicator 206 (in the vertical direction as shown in FIG. 4) may be less than the height of scale 200, which may increase the visual contrast between elastic-resistive WOB indicator 206 and scale 200.

In some embodiments, the overall (or exterior) size and/or shape of elastic-resistive WOB indicator 206 remain constant, while the relative sizes of component portions 220 and 222 adjust dynamically. In other embodiments, the overall (or exterior) size and/or shape of elastic-resistive WOB indicator 206 may change over time. For example, in embodiments in which elastic-resistive WOB indicator 206 comprises a bar graph (e.g., extending from the left edge of scale 200), the horizontal length of elastic-resistive WOB indicator 206 may be dynamic.

In some embodiments, scale 200 may include a set of numerical indices 240 to quantify the range of WOB values for each sector 210-216. Such values may have any suitable units, e.g., Joules (J), Joules per liter (J/L), Joules per minute (J/min) (i.e., power), or Joules per minute per kilogram (J/min/kg) (i.e., normalized power). The particular values defined by numerical indices 240 (and thus, the ranges of each sector 210-216) may be determined based on any suitable data, e.g., historical data. In some embodiments, the values defined by numerical indices 240 may be permanent for WOB graphic 16 a. In other embodiments, the values defined by numerical indices 240 may be configurable and/or adjustable by an operator. In addition, different numerical indices 240 having different values may be used for different patients, different respiratory management protocols, or for any other varying parameter(s).

One example set of numerical indices 240 is shown in FIG. 4. In this example, suppose that a normal acceptable range for a patient's WOB ($WOB_{PATIENT}$) is typically 0.3 J/L to 0.7 J/L. Thus, the range from 0 J/L to 0.3 J/L may be deemed subnormal. Thus, unless there are particular reasons for allowing a patient's WOB to fall below 0.3 J/L, a $WOB_{PATIENT}$ reading consistently remaining below 0.3 J/L could signal to the caregiver that the patient's management protocol should be reconsidered. Further, suppose that values falling above 0.70 J/L are generally above an acceptable level. Thus, unless there are particular reasons for allowing a patient's WOB to rise above 0.7 J/L, a $WOB_{PATIENT}$ reading consistently remaining above 0.7 J/L could signal to the caregiver that the patient's management protocol should be reconsidered. Further, suppose that values falling above 1.0 J/L are deemed to be particularly cautionary or potentially harmful. Thus, unless there are particular reasons for allowing a patient's WOB to rise above 1.0 J/L, a $WOB_{PATIENT}$ reading consistently remaining above 1.0 J/L could signal to the caregiver that the patient's management protocol is particularly cautionary or potentially harmful and should thus be reconsidered.

Thus, in this example, the set of numerical indices 240 includes the values 0, 0.3, 0.7, 1.0, and 2.0 positioned proximate the corresponding sector transition lines 230-238. A graphic representation of the unit of measurement, e.g., Joules/liter (J/L), may be included, as shown in FIG. 4, or may be omitted. Numerical indices 240 may be otherwise positioned and/or configured to correspond to appropriate sector transitions or other points within sectors 210-216 of WOB graphic 16 a.

In some embodiments, WOB graphic 16 a may include a WOB units selector 242 (e.g., a button) providing an interface allowing an operator to select from multiple units for which to display WOB measures on WOB graphic 16 a. For example, selecting button 242 may open a window allowing the user to select from different units—e.g., Joules (J), Joules per liter (J/L), Joules per minute (J/min), or Joules per minute per kilogram (J/min/kg)—for which WOB measures are displayed in WOB graphic 16 a. When an operator selects a particular unit, the values and/or units displayed in numerical indices 240 may be automatically updated as appropriate. In this manner, this operator may select a desired units setting for WOB measures displayed in WOB graphic 16 a.

Like scale 200, elastic-resistive WOB indicator 206 may be configured such that indicator portions 220 and 222 are visibly discernable from each other, such that a caregiver can quickly and easily identify the relative magnitudes of $WOB_{PATIENT-ELASTIC}$ and $WOB_{PATIENT-RESISTIVE}$. In some embodiments, indicator portions 220 and 222 are shaded in two different colors (or two different shades of the same basic color). However, it should be understood that indicator portions 220 and 222 may be otherwise colored or shaded, or may not be colored or shaded at all.

Indicator portions 220 and 222 may be divided by a reader 250, which may dynamically move within elastic-resistive WOB indicator 206 (e.g., to the left or right) to adjust the relative sizes of indicator portions 220 and 222 as the relative magnitude and/or percentage of the resistive and elastic WOB components change over time. In some embodiments, reader 250 may double as, or be otherwise associated with $WOB_{PATIENT}$ indicator 204. In other embodiments, reader 250 may be distinct from $WOB_{PATIENT}$ indicator 204. In other embodiments, a leading or trailing line of elastic-resistive WOB indicator 206, or any other appropriate graphic representation within or associated with elastic-resistive WOB indicator 206, may serve as $WOB_{PATIENT}$ indicator 204. For example, the leading end (here, the right-most boundary or indicator portion 222) may serve as $WOB_{PATIENT}$ indicator 204.

In other embodiments, elastic-resistive WOB indicator 206 may simply comprise a line or other suitable indicating means, and the patient's resistive and/or elastic WOB components may be graphically displayed separately, as numerical values of an appropriate unit of measure, or in any other suitable manner.

In some embodiments of the present disclosure, the caregiver may be able to easily identify the relative percentages of the patient's resistive work and elastic work from indicator portions 220 and 222, respectively, of elastic-resistive WOB indicator 206. By dividing elastic-resistive WOB indicator 206 into resistive and elastic WOB components 220 and 222, a caregiver may be able to easily determine whether a patient is exerting too much or too little resistive or elastic work, which in turn may assist the caregiver in diagnosing the patient's condition and/or adjusting the ventilation strategy.

Figure 6:
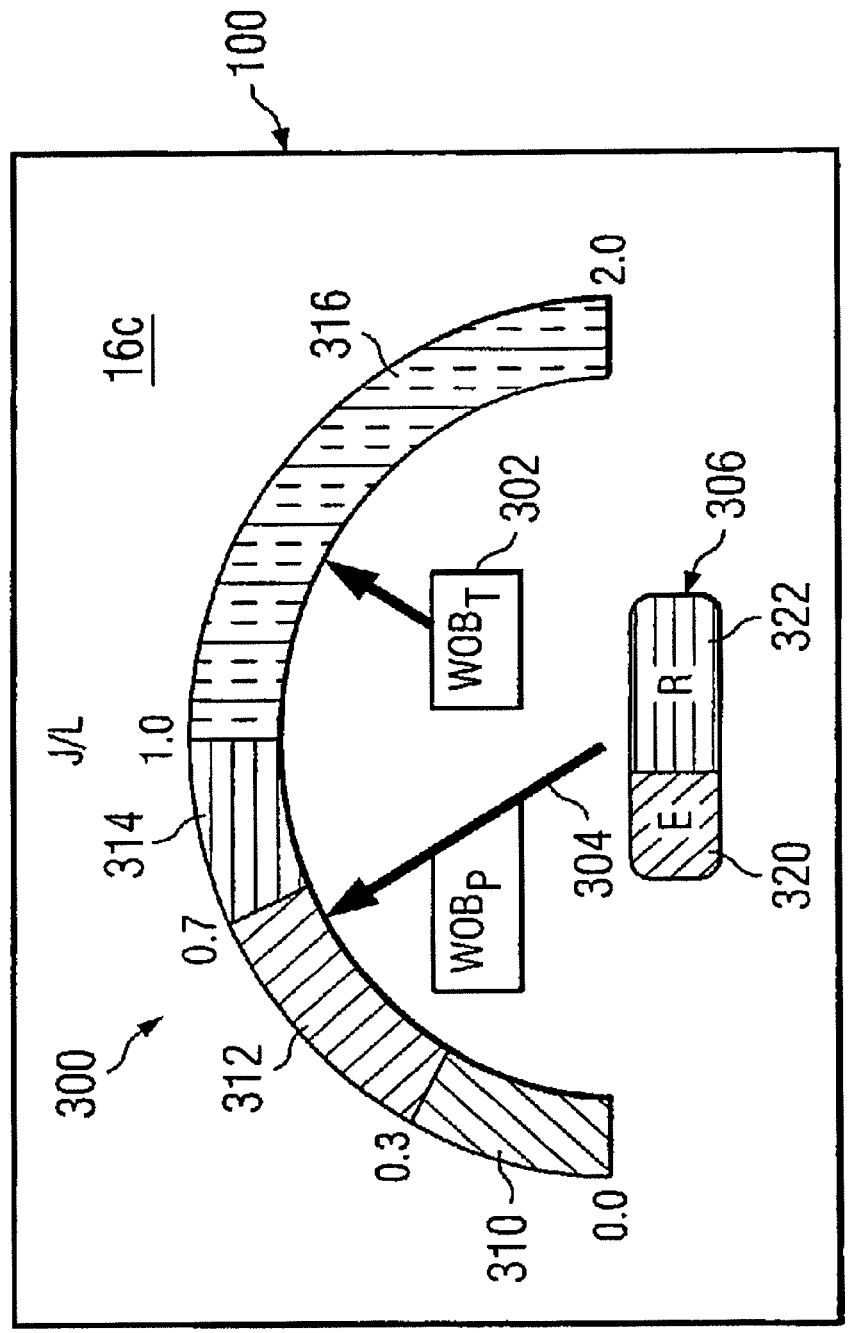
FIG. 6 illustrates a third example graphic work of breathing graphic, according to another embodiment of the disclosure.

In some embodiments, WOB graphic 16a may include one or more display legends that may include any desired graphical representations to assist the caregiver in better understanding WOB graphic 16a. For example, as shown in FIG. 4, a display legend 260 may indicate that indicator portions 220 and 222 of elastic-resistive WOB indicator 206 represent the elastic WOB component (illustrated as "$WOB_E$") and the resistive WOB component (illustrated as "$WOB_R$"), respectively, of the patient's WOB. In other embodiments, symbols or legends indicating that indicator portions 220 and 222 represent the elastic and resistive WOB components may be located in or adjacent to indicator portions 220 and 222 (such as shown in the embodiment of FIG. 6, for example). Similarly, display legend 260 or another display legend may explain the color-coding of sectors 210-216 of scale 200.

Figure 5:
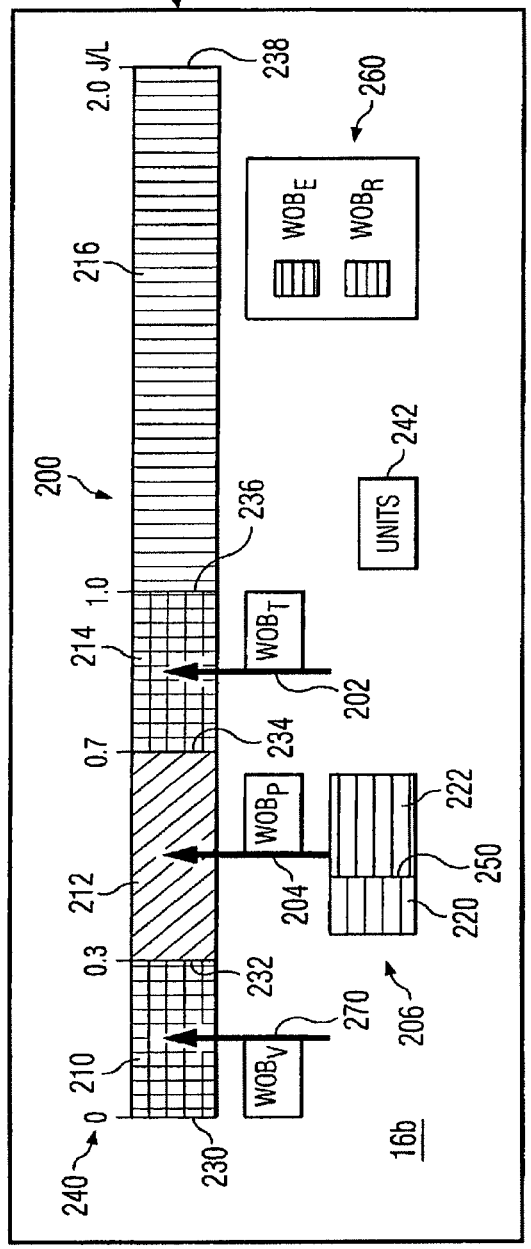
FIG. 5 illustrates a second example graphic work of breathing graphic, according to one embodiment of the disclosure.

FIG. 5 illustrates another example of a WOB graphic 16b on a display device 100, according to one embodiment of the disclosure. WOB graphic 16b may be similar to WOB graphic 16a shown in FIG. 4 and discussed above, but may additionally include a $WOB_{VENTILATOR}$ indicator 270 that indicates a measure of the ventilator's WOB. $WOB_{VENTILATOR}$ indicator 270 may comprise any pointer or other graphic that may advance and retreat along scale 200 as the $WOB_{VENTILATOR}$ changes over time. $WOB_{VENTILATOR}$ indicator 270 may include any suitable label or other identifier. In some embodiments, $WOB_{VENTILATOR}$ indicator 270 may include a numerical indication of the current $WOB_{VENTILATOR}$ measure. In other embodiments, no such numerical indication is displayed.

FIG. 6 illustrates another example of a WOB graphic 16c on a display device 100, according to another embodiment of the disclosure. WOB graphic 16c may include a scale 300, a $WOB_{TOTAL}$ indicator 302 for indicating a measure of the total WOB, a $WOB_{PATIENT}$ indicator 304 for indicating a measure of the patient's WOB, and/or an elastic-resistive WOB indicator 306 for indicating the elastic and resistive WOB components of the patient's WOB.

Scale 300 and indicators 302-306 may be analogous to scale 200 and indicators 202-206 shown in FIG. 4. Scale 300 may extend in an arc, and may be divided into sections 310-316, which may be similar to sections 210-216 discussed above. $WOB_{TOTAL}$ indicator 302 may comprise a pointer that rotates relative to curved scale 300 to indicate a measure of the total WOB. Similarly, $WOB_{PATIENT}$ indicator 304 may comprise a pointer that rotates relative to curved scale 300 to indicate a measure of the patient's WOB.

Elastic-resistive WOB indicator 306 may be divided into indicator portions 320 and 322, which may indicate the elastic and resistive WOB components of the patient's WOB, e.g., as discussed above regarding indicator portions 220 and 222 of elastic-resistive WOB indicator 206. The relative sizes (e.g., the length and/or width) of indicator portions 320 and 322 may dynamically change to indicate the current relative measures of elastic and resistive WOB components, e.g., as discussed above regarding elastic-resistive WOB indicator 206. However, unlike elastic-resistive WOB indicator 206, elastic-resistive WOB indicator 306 may remain stationary (rather than moving along scale 300). In addition, in some embodiments, an indication that indicator portions 320 and 322 represent the elastic and resistive WOB components is located in or adjacent to indicator portions 320 and 322. For example, as shown in FIG. 6, the letters "E" and "R" may be displayed in indicator portions 320 and 322 to indicate that that indicator portions 320 and 322 represent the elastic and resistive WOB components, respectively. In other embodiments, WOB graphic 16c may include one or more display legends to provide such information, e.g., as discussed above regarding display legend 260.

Figure 7:
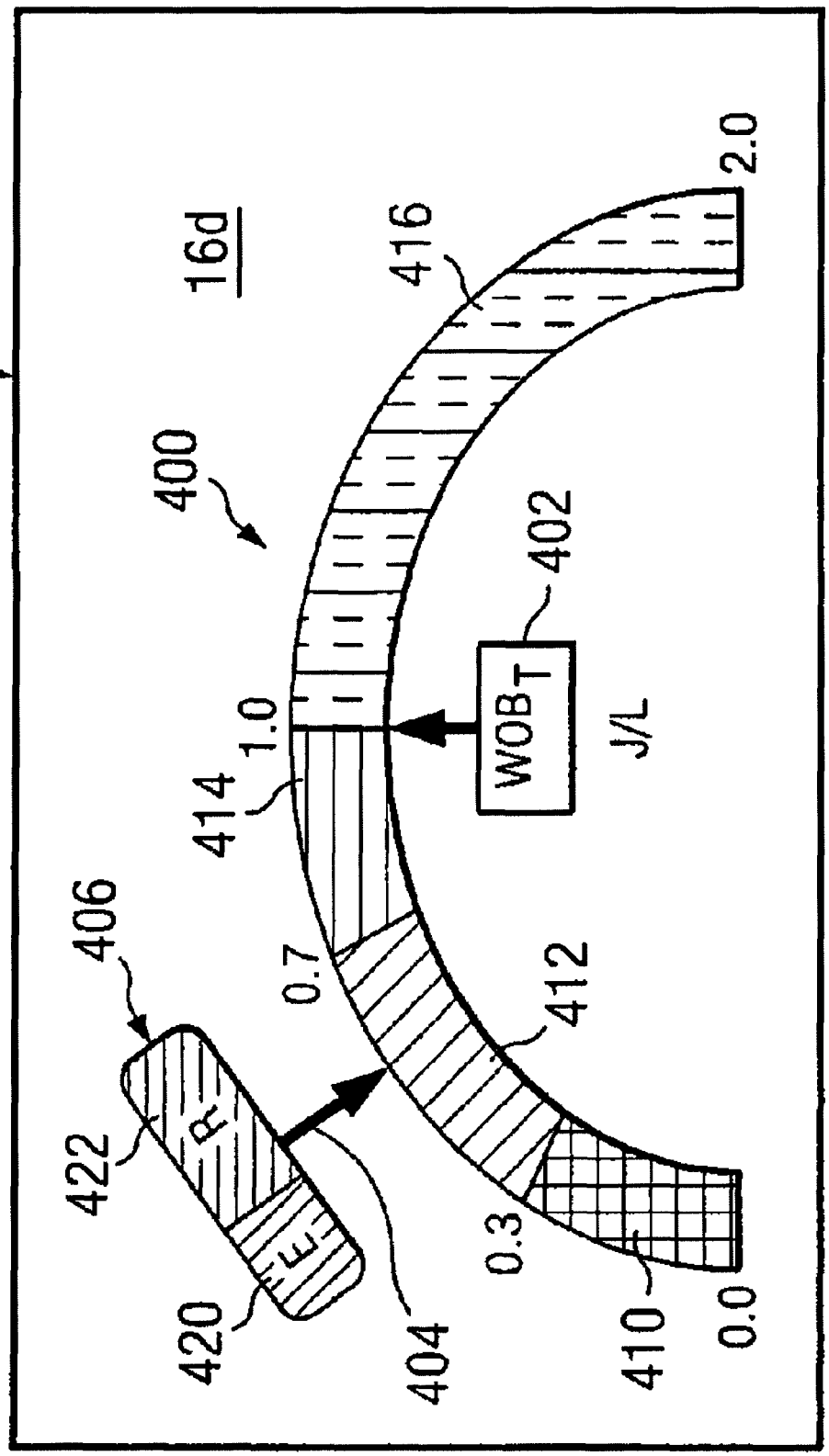
FIG. 7 illustrates a fourth example graphic work of breathing graphic, according to another embodiment of the disclosure.

FIG. 7 illustrates another example of a WOB graphic 16d on a display device 100, according to another embodiment of the disclosure. WOB graphic 16d may include a scale 400, a $WOB_{TOTAL}$ indicator 402 for indicating a measure of the total WOB, a $WOB_{PATIENT}$ indicator 404 for indicating a measure of the patient's WOB, and/or an elastic-resistive WOB indicator 406 for indicating the elastic and resistive WOB components of the patient's WOB. Scale 400 and indicators 402-406 may be analogous to scale 300 and indicators 302-306 shown in FIG. 6. For example, scale 400 may extend in an arc, and may be divided into sections 410-416. WOB TOTAL indicator 402 may move in an arced path along an inner perimeter of scale 400. In other embodiments, $WOB_{TOTAL}$ indicator 402 may move along an outer perimeter of scale 400. $WOB_{PATIENT}$ indicator 404 may move in an arced path along an outer scale 400, and may be coupled to elastic-resistive WOB indicator 406 such that elastic-resistive WOB indicator 406 moves along with $WOB_{PATIENT}$ indicator 404. In other embodiments, elastic-resistive WOB indicator 406 and/or $WOB_{PATIENT}$ indicator 404 may move along an inner perimeter of scale 400.

Elastic-resistive WOB indicator 406 may be divided into indicator portions 420 and 422, which may indicate the elastic and resistive WOB components of the patient's WOB. The relative sizes of indicator portions 420 and 422 may dynamically change to indicate the current relative measures of elastic and resistive WOB components, e.g., as discussed above regarding elastic-resistive WOB indicator 206. In addition, in some embodiments, an indication (e.g., the letters "E" and "R") that indicator portions 420 and 422 represent the elastic and resistive WOB components may be located in or adjacent to indicator portions 420 and 422, such as discussed above regarding FIG. 6.

Figure 8:
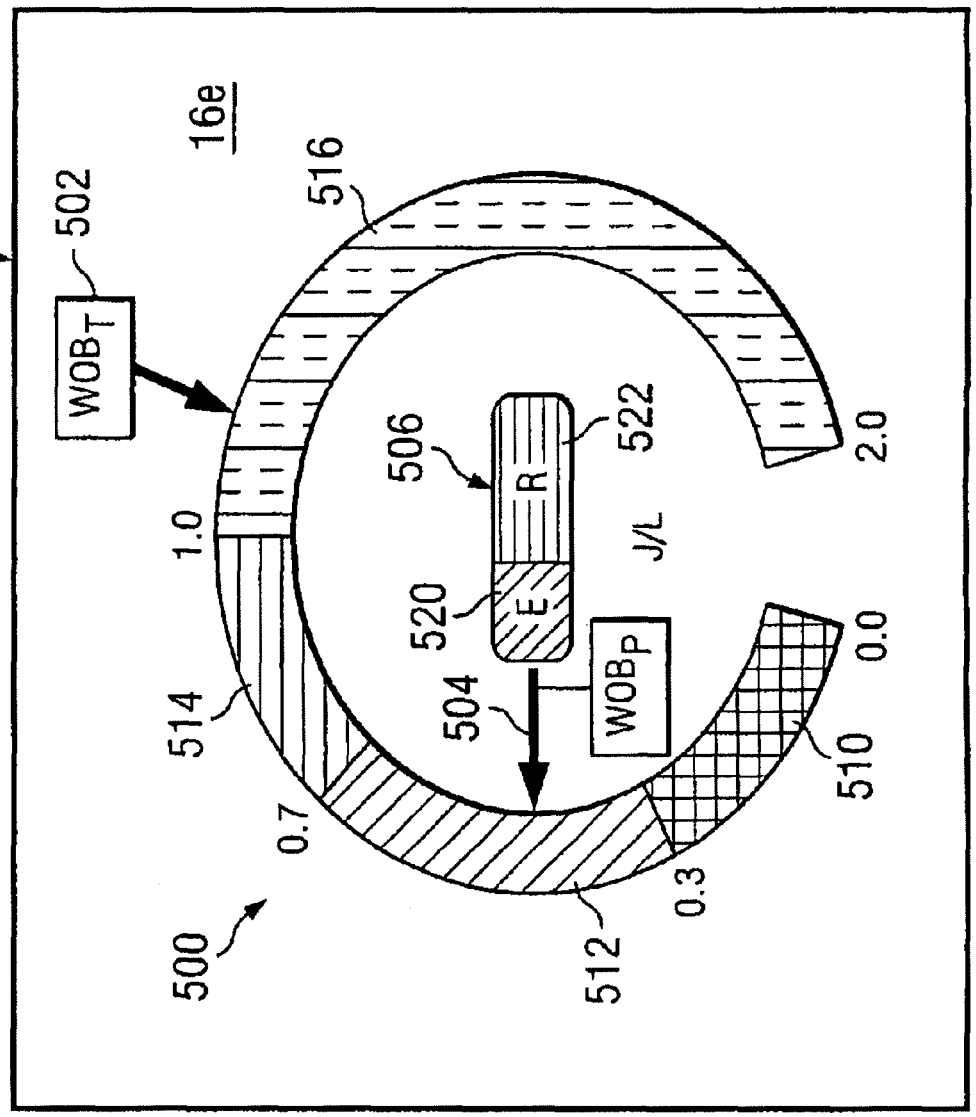
FIG. 8 illustrates a fifth example graphic work of breathing graphic, according to another embodiment of the disclosure.

FIG. 8 illustrates another example of a WOB graphic 16e on a display device 100, according to another embodiment of the disclosure. WOB graphic 16e may include a scale 500, a $WOB_{TOTAL}$ indicator 502 for indicating a measure of the total WOB, a $WOB_{PATIENT}$ indicator 504 for indicating a measure of the patient's WOB, and/or an elastic-resistive WOB indicator 506 for indicating the elastic and resistive WOB components of the patient's WOB. Scale 500 and indicators 502-506 may be analogous to scale 200 and indicators 202-206 shown in FIG. 4. Scale 500 may extend in an elliptical or other curved shape, and may be divided into sections 510-516. $WOB_{TOTAL}$ indicator 502 may move in a curved path along an outer perimeter of scale 500. In other embodiments, $WOB_{TOTAL}$ indicator 502 may move along an inner perimeter of scale 500. $WOB_{PATIENT}$ indicator 504 may move in a curved path along an inner scale 500. In other embodiments, $WOB_{PATIENT}$ indicator 504 may move along an outer perimeter of scale 500.

Elastic-resistive WOB indicator 506 may be divided into indicator portions 520 and 522, which may indicate the elastic and resistive WOB components of the patient's WOB. The relative sizes of indicator portions 520 and 522 may dynamically change to indicate the current relative measures of elastic and resistive WOB components. Like elastic-resistive WOB indicator 306 shown in FIG. 6, elastic-resistive WOB indicator 506 may remain stationary (rather than moving along scale 500). As discussed above, an indication (e.g., the letters "E" and "R") that indicator portions 520 and 522 represent the elastic and resistive WOB components may be located in or adjacent to indicator portions 520 and 522.

Figure 9:
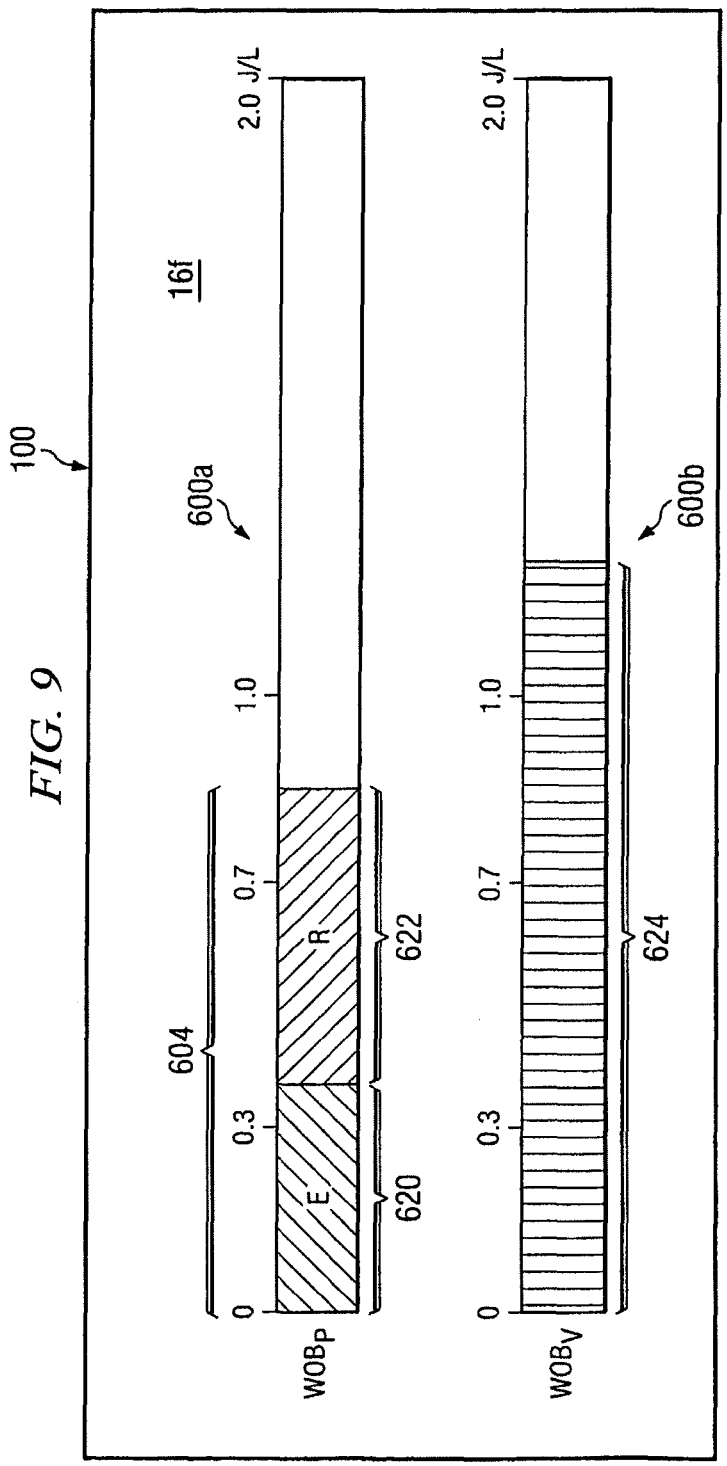
FIG. 9 illustrates a sixth example graphic work of breathing graphic, according to another embodiment of the disclosure.

FIG. 9 illustrates another example of a WOB graphic 16f on a display device 100, according to another embodiment of the disclosure. WOB graphic 16f may include one or more scales for indicating the patient's WOB ($WOB_{PATIENT}$), the ventilator's WOB ($WOB_{VENTILATOR}$), and/or the total WOB ($WOB_{TOTAL}$). For example, as shown in FIG. 9, WOB graphic 16f may include (a) a first scale 600a for indicating the patient's WOB ($WOB_{PATIENT}$) and/or the elastic and resistive WOB components of $WOB_{PATIENT}$, and (b) a second scale 600b for indicating the ventilator's WOB ($WOB_{VENTILATOR}$). In another embodiment, WOB graphic 16f may include a third scale for indicating the total WOB ($WOB_{TOTAL}$). In other embodiments, WOB graphic 16f may include any one, two or all three of such scales indicating $WOB_{PATIENT}$, $WOB_{VENTILATOR}$, and/or $WOB_{TOTAL}$.

Regarding scale 600a shown in FIG. 9, a $WOB_{PATIENT}$ indicator 604 in the form of a bar may advance and retreat along scale 600a to indicate a measure of the patient's WOB, $WOB_{PATIENT}$. $WOB_{PATIENT}$ indicator 604 may be divided into indicator portions 620 and 622, which may indicate the elastic and resistive WOB components of the patient's WOB, respectively. The sizes of indicator portions 620 and 622 may dynamically change to indicate the current relative measures of elastic and resistive WOB components. An indication (e.g., the letters "E" and "R") that indicator portions 620 and 622 represent the elastic and resistive WOB components may be located in or adjacent to indicator portions 620 and 622. Alternatively, WOB graphic 16f may include a legend (e.g., as discussed above with respect to FIG. 4) to indicate that portions 620 and 622 represent the elastic and resistive WOB components of the patient's WOB. Indicator portions 620 and 622 may be color-coded or otherwise visually distinct, e.g., as described above. Scale 600a may include a set of numerical indices (e.g., similar to numerical indices 240 shown in FIG. 4) to quantify ranges of WOB values for pre-determined sectors of scale 600a (e.g., 0 to 0.3, 0.3 to 0.7, 0.7 to 1.0, and 1.0 to 2.0).

Regarding scale 600b, a $WOB_{VENTILATOR}$ indicator 624 in the form of a bar may advance and retreat along scale 600b to indicate a measure of the ventilator's WOB, $WOB_{VENTILATOR}$. $WOB_{VENTILATOR}$ indicator 624 may be color-coded or otherwise visually distinct from indicator portions 620 and 622 of $WOB_{PATIENT}$ indicator 604. In other embodiments, WOB graphic 16f may not include scale 600b or $WOB_{VENTILATOR}$ indicator 624. Like scale 600a, scale 600b may include a set of numerical indices to quantify ranges of WOB values for pre-determined sectors of scale 600b. In other embodiments, scales 600a and 600b may share a common set or numerical indices, or may not include numerical indices.

Although the disclosed embodiments have been described in detail, it should be understood that various changes, substitutions and alterations can be made herein without departing from the spirit and scope of the disclosure as illustrated by the following claims.

Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software or firmware components described herein as would be understood by those skilled in the art now and hereafter.

While various embodiments have been described, various changes and modifications may be made which are well within the scope of the present disclosure. Numerous other changes may be made which will readily suggest themselves to those skilled in the art and which are encompassed in the spirit of the disclosure and as defined in the claims.

What is claimed is:

1. A breathing support system, comprising:
   a breathing support device configured to deliver gas to a patient;
   a software-generated graphic indicating one or more measures regarding the patient's work of breathing;
   a display device associated with the breathing support device, the display device configured to display the software-generated graphic,
   wherein the software-generated graphic includes:
   a scale in a form of a bar with a single axis representing a range of work of breathing values; and
   one or more work of breathing indicators that move relative to the scale.

2. The system according to claim 1, further comprising a work of breathing calculation module configured to receive data from one or more sensors and calculate the one or more measures using one or more work of breathing algorithms.

3. The system according to claim 2, wherein the data received by the work of breathing calculation module comprises data regarding delivery of gas to the patient, including at least one of pressure and flow of gas delivered to the patient.

4. The system according to claim 2, wherein the work of breathing calculation module is configured to receive data from one or more sensors associated with an artificial airway inserted in the patient.

5. The system according to claim 1, further comprising:
   one or more sensors configured to obtain data regarding the patient's breathing;
   a memory device storing one or more work of breathing algorithms; and
   a processor communicatively coupled to the one or more sensors and the memory device and configured to determine the one or more measures regarding the patient's work of breathing based at least on data obtained by the one or more sensors and the one or more work of breathing algorithms.

6. The system according to claim 5, wherein the one or more sensors are associated with an artificial airway inserted in the patient.

7. The system according to claim 5, wherein the one or more sensors are not associated with an artificial airway inserted in the patient.

8. The system according to claim 1, wherein the display device is at least partially integrated with the breathing support device.

9. The system according to claim 1, wherein the display device is physically separate from the breathing support device.

10. The system according to claim 1, wherein the software-generated graphic includes:
a total work of breathing indicator indicating a measure of the patient's total work of breathing, the total work of breathing comprising a patient work of breathing component and a device work of breathing component, the patient work of breathing component comprising the portion of the total work of breathing provided by the patient and the device work of breathing component comprising the portion of the total work of breathing provided by the breathing support device.

11. The system according to claim 1, wherein the software-generated graphic further includes an indication of an elastic work of breathing component relative to a resistive work of breathing component.

12. The display according to claim 1, wherein the one or more measures comprise one or more estimated measures regarding the patient's work of breathing.

13. The system according to claim 1, wherein the software-generated graphic includes:
an elastic-resistive indicator indicating a measure of the elastic work of breathing component relative to a measure of the resistive work of breathing component.

14. The system according to claim 1, wherein the software-generated graphic includes:
an elastic-resistive graphic including a first portion and a second portion, the first portion indicating a measure of an elastic work of breathing component and the second portion indicating a measure of a resistive work of breathing component; and
wherein relative sizes of the first and second portions of the elastic-resistive graphic dynamically adjust to indicate the measure of the elastic work of breathing component relative to the measure of the resistive work of breathing component.

15. The system according to claim 14, wherein the size of the elastic-resistive graphic remains constant as the relative sizes of the first and second portions dynamically adjust.

16. The system according to claim 1, wherein the work of breathing value is Joules per minute (J/min) or Joules per Liter (J/L).

17. A breathing support system, comprising:
a breathing support device configured to deliver gas to a patient;
a software-generated graphic indicating one or more measures regarding the patient's work of breathing;
a display device associated with the breathing support device, the display device configured to display the software-generated graphic, and
wherein the software-generated graphic includes:
an elastic-resistive graphic including a first portion and a second portion, the first portion indicating a measure of an elastic work of breathing component and the second portion indicating a measure of a resistive work of breathing component; and
wherein relative sizes of the first and second portions of the elastic-resistive graphic dynamically adjust on a bar to indicate the measure of the elastic work of breathing component relative to the measure of the resistive work of breathing component.

18. The system according to claim 17, wherein the size of the elastic-resistive graphic remains constant as the relative sizes of the first and second portions dynamically adjust.

19. The system according to claim 17, further comprising a work of breathing calculation module configured to receive data from one or more sensors and calculate the one or more measures regarding the patient's work of breathing using one or more work of breathing algorithms.

20. The system according to claim 19, wherein the data received by the work of breathing calculation module comprises data regarding delivery of gas to the patient, including at least one of pressure and flow of gas delivered to the patient.

21. The system according to claim 17, further comprising:
one or more sensors configured to obtain data regarding the patient's breathing;
a memory device storing one or more work of breathing algorithms; and
a processor communicatively coupled to the one or more sensors and the memory device and configured to determine the one or more measures based at least on data obtained by the one or more sensors and the one or more work of breathing algorithms.

* * * * *